United States Patent
Gil et al.

(10) Patent No.: US 7,275,544 B2
(45) Date of Patent: *Oct. 2, 2007

(54) COVERING FOR AN ASEPTIC TREATMENT SITE

(76) Inventors: Michael Gil, 117 Garden Ct. Dr., West Point, MS (US) 39773; Joseph Hare, 953 E. 43rd Ave., Spokane, WA (US) 99203; Judson E. Threlkeld, 19503 NE. 6th, Camas, WA (US) 98607

( * ) Notice: Subject to any disclaimer, the term of this patent is extended or adjusted under 35 U.S.C. 154(b) by 0 days.

This patent is subject to a terminal disclaimer.

(21) Appl. No.: 11/298,251

(22) Filed: Dec. 9, 2005

(65) Prior Publication Data

US 2006/0207609 A1    Sep. 21, 2006

Related U.S. Application Data

(63) Continuation-in-part of application No. PCT/US2004/039893, filed on Nov. 30, 2004, and a continuation-in-part of application No. 10/726,324, filed on Dec. 1, 2003.

(51) Int. Cl.
*A61F 19/00* (2006.01)
*A61B 19/08* (2006.01)

(52) U.S. Cl. .................. 128/849; 128/853; 128/854

(58) Field of Classification Search ............. 128/849, 128/853, 854, 888, 897; 602/41–45; 18/854; 225/39–42
See application file for complete search history.

(56) References Cited

U.S. PATENT DOCUMENTS

| 3,799,161 A | 3/1974 | Collins |
| 3,826,253 A | 7/1974 | Larsh et al. |
| 3,916,887 A | 11/1975 | Kelly |
| 4,027,665 A | 6/1977 | Scrivens |
| 4,378,794 A | 4/1983 | Collins |
| 4,414,968 A | 11/1983 | Amin |
| 4,433,026 A | 2/1984 | Molde |
| 4,462,396 A | 7/1984 | Wichman |
| 4,471,769 A | 9/1984 | Lockhart |
| 4,690,137 A | 9/1987 | Starzmann |
| 5,151,314 A | 9/1992 | Brown |
| 5,161,544 A | 11/1992 | Morris |
| 5,197,493 A * | 3/1993 | Grier-Idris .................. 128/853 |
| 5,354,261 A | 10/1994 | Clark et al. |
| 5,372,589 A | 12/1994 | Davis |
| 5,445,165 A | 8/1995 | Fenwick |
| 5,538,012 A * | 7/1996 | Wiedner et al. ............. 128/853 |
| 5,562,107 A * | 10/1996 | Lavender et al. ........... 128/888 |
| 5,702,356 A * | 12/1997 | Hathman ..................... 602/41 |

(Continued)

FOREIGN PATENT DOCUMENTS

GB    2326100    12/1998

(Continued)

*Primary Examiner*—Patricia Bianco
*Assistant Examiner*—Brandon Jackson
(74) *Attorney, Agent, or Firm*—Withers & Keys, LLC

(57) ABSTRACT

A covering for an aseptic treatment site is disclosed. An exemplary covering includes a substrate defining an aperture which permits selective access to an aseptic treatment site on a patient; and a transparent cover is borne by the substrate and which is removably affixed in substantially aseptic covering relation relative to the aperture.

27 Claims, 12 Drawing Sheets

U.S. PATENT DOCUMENTS

| | | |
|---|---|---|
| 5,975,082 A * | 11/1999 | Dowdy ..................... 128/849 |
| 6,105,579 A | 8/2000 | Levitt et al. |
| 6,199,553 B1 | 3/2001 | Hafer et al. |
| 6,357,445 B1 | 3/2002 | Shaw |
| 6,382,212 B1 | 5/2002 | Borchard |
| 6,530,376 B1 | 3/2003 | Padget et al. |
| 6,564,803 B2 | 5/2003 | Lofgren |
| 6,966,320 B1 | 11/2005 | Baynes |
| 2002/0108615 A1* | 8/2002 | Levitt et al. ................ 128/853 |
| 2003/0009122 A1* | 1/2003 | Veras ........................ 602/42 |
| 2003/0060831 A1 | 3/2003 | Bonutti |
| 2003/0113827 A1 | 6/2003 | Burkoth |
| 2003/0121522 A1 | 7/2003 | Gingles et al. |
| 2003/0196668 A1 | 10/2003 | Harrision et al. |
| 2004/0103904 A1 | 6/2004 | Auerbach et al. |
| 2006/0207609 A1 | 9/2006 | Gil et al. |

FOREIGN PATENT DOCUMENTS

WO    WO 2005/053754    6/2005

* cited by examiner

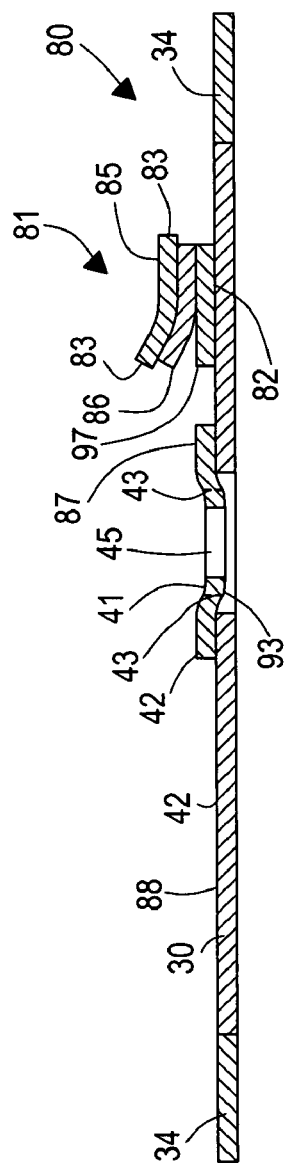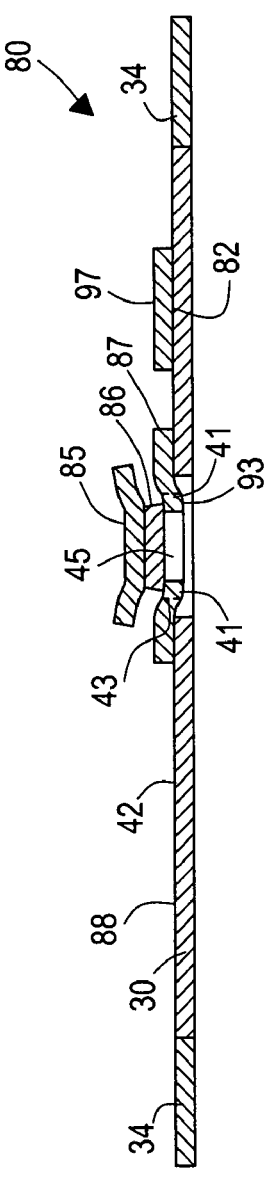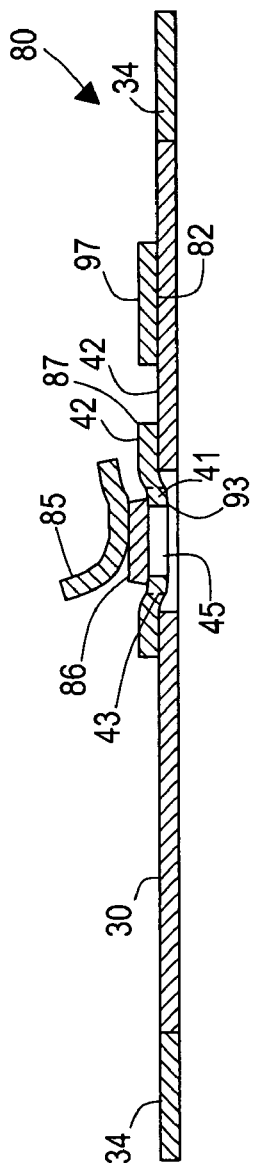

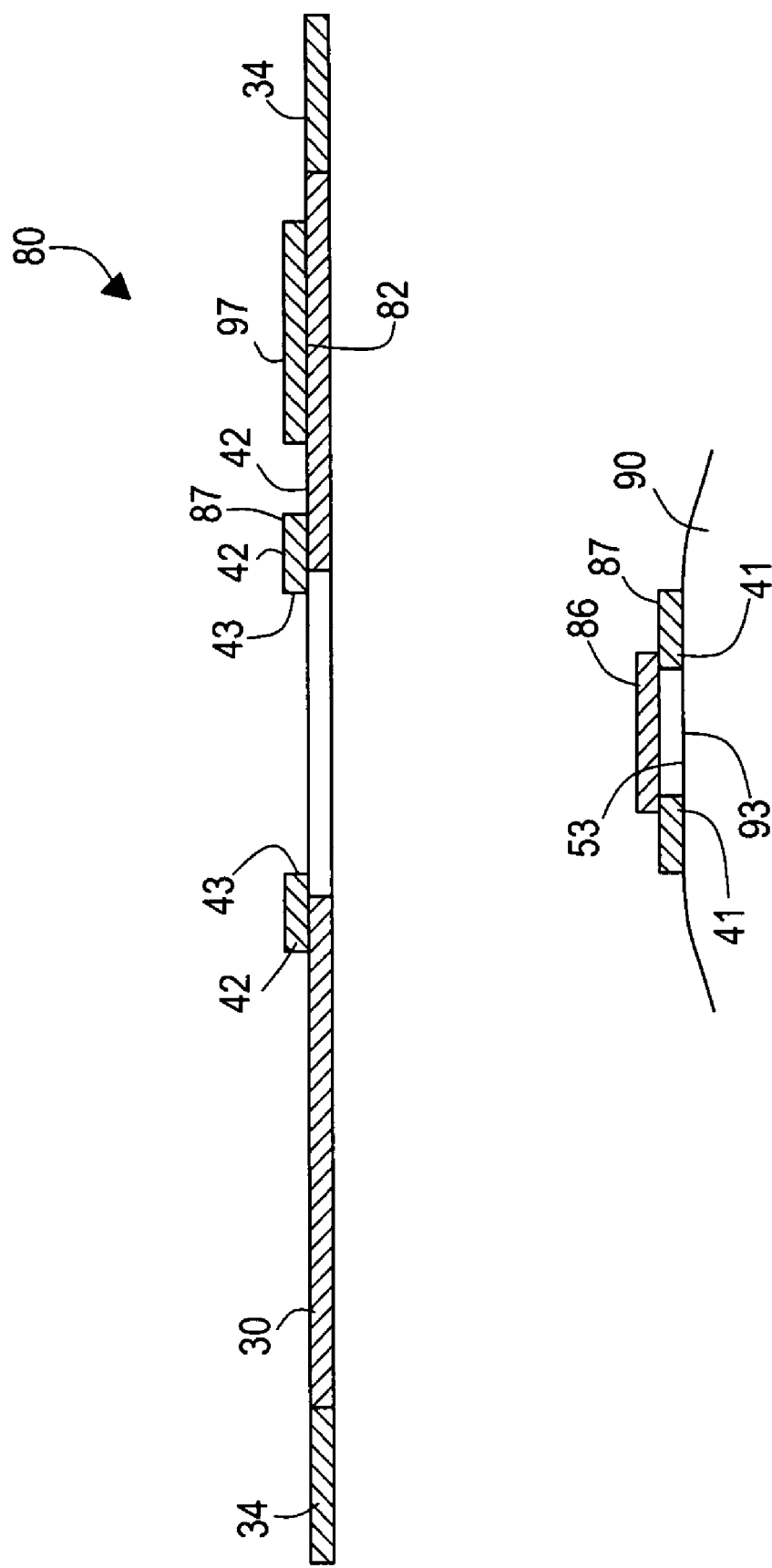

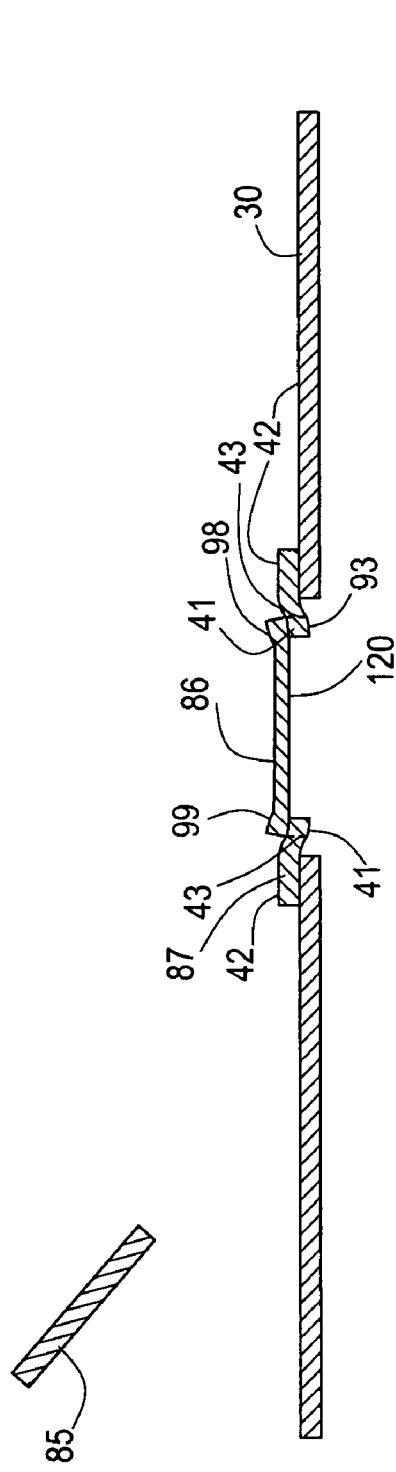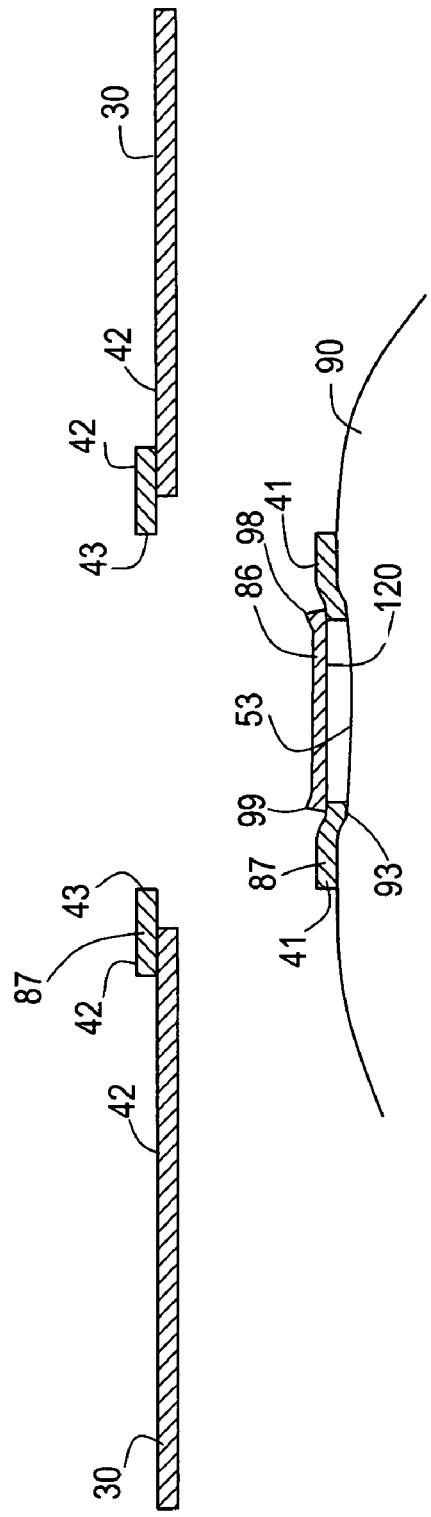

COVERING FOR AN ASEPTIC TREATMENT SITE

CROSS-REFERENCE TO RELATED APPLICATIONS

This patent application (i) claims the benefit of priority to and is a continuation-in-part of International Patent Application Serial No. PCT/US04/39893 filed on Nov. 30, 2004, and (ii) claims the benefit of priority to and is a continuation-in-part of U.S. patent application Ser. No. 10/726,324, filed on Dec. 01, 2003, the subject matter of both of which is hereby incorporated by reference in its entirety.

TECHNICAL FIELD

The present invention relates to a covering for an aseptic treatment site, and more specifically to a fenestrated surgical drape, which has a portion that may remain in place after a surgical intervention and which will permit a clinician to continually observe and access, if necessary, the aseptic treatment site.

BACKGROUND OF THE INVENTION

The prior art is replete with numerous examples of surgical drapes, which have been designed and utilized through the years to aid clinicians in the treatment of patients having various maladies. Typically, such surgical drapes have been adapted for use with a wide variety of electronic and mechanical devices, which are used for treating the patient's medical conditions. Depending on the nature of the condition, such medical devices can, for example, be surgically implanted, connected externally to the patient receiving treatment, or even used during a surgical technique.

Fenestrated surgical drapes have been used, heretofore, to maintain sterile conditions, maintain patient privacy, absorb bodily fluids, and/or further provide a clear and clean work area for the clinician. The prior art surgical drapes, such as the one shown in FIG. 1, employ a fenestration or opening in the surgical drape, which provides the clinician with access to the desired site on the patient's body while preserving the function of the surgical drape, which is utilized to cover other areas of the patient's body.

In a typical utilization of such fenestrated surgical drapes, a medical treatment site, such as a surgical site, is located and thereafter the site is prepared for surgery by making it substantially aseptic. Thereafter, the surgical drape having a fenestration is placed over the surgical site and the medical procedure or surgery is initiated. Following completion of the surgery, the typical practice is to remove the entire surgical drape because portions of the drape may have absorbed body fluid during the surgery. The patient is then moved from the surgical theater to a recovery room. Some surgical procedures require that the surgical site be monitored for a period of time in order to detect any abnormalities in the recovery of the patient. On some occasions, irregularities may occur either at the surgical site or elsewhere in the patient's body, which indicate that the previous surgical procedure has been unsuccessful or another situation has arisen in the patient's body, which indicates that further surgical intervention is required by the clinician. In these circumstances, immediate surgical intervention is not possible inasmuch as the original surgical site is no longer in an aseptic condition. Consequently under these conditions, the surgical site must be again rendered aseptic before a clinician can gain access to same. This time delay to render a surgical site aseptic can be significant, and may under some circumstances by life threatening.

Therefore, a covering for an aseptic treatment site, which addresses the perceived shortcomings of the prior art practices and devices utilized heretofore is the subject matter of the present application.

SUMMARY OF THE INVENTION

The present invention is directed to drapes suitable for use in an operating room setting. The drapes of the present invention address one or more of the above-mentioned deficiencies in the art. In particular, the drapes of the present invention provide one or more of the following features: (i) a covering for an aseptic treatment site, (ii) a covering for an aseptic treatment site, wherein the covering is detachable from the drape, (iii) a covering for an aseptic treatment site, wherein the covering comprises a transparent cover that is removably affixed to a portion of the drape so as to provide access to the aseptic treatment site, (iv) a covering for an aseptic treatment site, wherein the covering comprises a transparent cover that provides visual inspection of the aseptic treatment site, and (v) a cover assembly attached to a portion of the drape, wherein one or more components of the cover assembly may be used to cover and protect an aseptic treatment site on a patient.

In one exemplary embodiment, the present invention is directed to a drape comprising a first region having a first region outer periphery and at least one fenestration positioned within the first region outer periphery, wherein the first region is suitable for covering an aseptic treatment site so that the aseptic treatment site is accessible through the at least one fenestration; and a second region surrounding the outer first region periphery of the first region, the second region being detachably joined to the first region such that detachment of the second region from the first region does not alter an outer periphery of the at least one fenestration.

In a further exemplary embodiment, the present invention is directed to a covering for an aseptic treatment site, wherein the covering includes (i) a substrate defining an aperture, which permits selective access to an aseptic treatment site on a patient; and (ii) a transparent cover borne by the substrate and which is removably affixed in substantially aseptic covering relation relative to the aperture.

In a further exemplary embodiment, the present invention is directed to a covering for an aseptic treatment site, wherein the covering includes (i) a flexible substrate having opposite first and second surfaces, and which defines an aperture which permits access to an aseptic treatment site on a patient; (ii) a first adhesive region borne on the second surface of the flexible substrate, and which substantially surrounds the aperture; (iii) a flexible transparent cover moveably affixed on the first surface of the flexible substrate, and which is moveable along a course of travel between a first, covering position relative to the aperture, and which permits observation of the aseptic treatment site, to a second, uncovered position relative to the aperture, and which permits access to the aseptic treatment site; and (iv) a second adhesive region borne by the flexible, transparent cover, and which releasably adhesively affixes the flexible transparent cover to the first surface of the flexible substrate.

In yet a further exemplary embodiment, the present invention is directed to a covering for an aseptic treatment site, wherein the covering includes (i) a flexible substrate having a first region and a releasably detachable second region, and wherein the first region defines an aperture which permits access to an aseptic treatment site on a patient; (ii) a first adhesive region substantially surrounding the aperture, and which is borne by the first region, and wherein the first adhesive region releasably adhesively affixes the first region on the body of the patient in the orientation such that the first region surrounds the aseptic treatment site; (iii) a flexible transparent cover hingedly affixed on the first surface of the flexible substrate, and wherein the transparent cover has a peripheral edge, opposite first and second surfaces, and opposite first and second ends, and wherein the second end of the flexible transparent cover is hingedly affixed on the first surface, and wherein the first end is moveable along a substantially arcuately shaped path of travel between a first position, wherein the transparent cover is disposed in a covering relation relative to the aperture and substantially out of direct contact with the aseptic treatment site to a second position, wherein the transparent cover is disposed in an orientation, which allows access to the aseptic treatment site by way of the aperture; and (iv) a second adhesive region disposed on either one of the transparent cover or the substrate and which releasably adhesively affixes the peripheral edge of the transparent cover on the substrate and in the first covering position relative to the aperture, and wherein the second adhesive region releases the transparent cover from the first position when force is applied to the first end of the transparent cover, and wherein the second adhesive region permits the transparent cover to be repeatedly moved between the first and second positions without substantially adhesively detaching the first adhesive region from the patient.

In yet a further embodiment, the present invention is directed to a drape having a cover assembly on a first location of the drape, wherein portions of the cover assembly may be used to cover and protect an aseptic treatment site on a patient. In one exemplary embodiment, the drape comprises a first region having a first region outer periphery and at least one fenestration positioned within the first region outer periphery, wherein the first region is suitable for covering an aseptic treatment site so that the aseptic treatment site is accessible through the at least one fenestration; and a cover assembly located on a first location of the drape, wherein the cover assembly comprises (i) a first release liner, and (ii) a transparent cover having a transparent cover outer periphery and being releasably attached to the first release liner, wherein the transparent cover has a first adhesive layer on an outer surface of the transparent cover, which is temporarily protected by the first release liner, the first adhesive layer being bonded to the drape at the first location. The cover assembly may further comprise a second release liner attached to the first location of the drape to protect the adhesive layer on the transparent cover.

The cover assembly may be positioned at a first location of the drape, wherein the first location is any location on the drape. In one exemplary embodiment, the first location is an area proximate a fenestration in the drape. In this exemplary embodiment, a portion of the transparent cover may be attached to the first location such that the step of removing the first release liner and adhesively bonding the transparent cover to a second location on the drape to surround the aseptic treatment site on the patient requires minimal effort on the part of a user.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein:

FIGS. 9A-9D depict a cross-sectional view of the exemplary drape of FIG. 7 illustrating steps for applying one or more components of an exemplary cover assembly over an aseptic treatment site;

FIGS. 12A-12D depict a cross-sectional view of the exemplary drape of FIG. 10 illustrating steps for applying one or more components of an exemplary cover assembly over an aseptic treatment site.

DETAILED DESCRIPTION OF THE INVENTION

The present invention is directed to coverings for an aseptic treatment site and operating room drapes containing the same. The present invention is further directed to methods of using coverings and operating room drapes containing the same during an operating room procedure so as to cover an aseptic treatment site, and maintain the treatment site in an aseptic condition following an intervention procedure. One exemplary covering of the present invention suitable for covering an aseptic treatment site is shown as exemplary covering 10 in FIG. 2.

Figure 1:
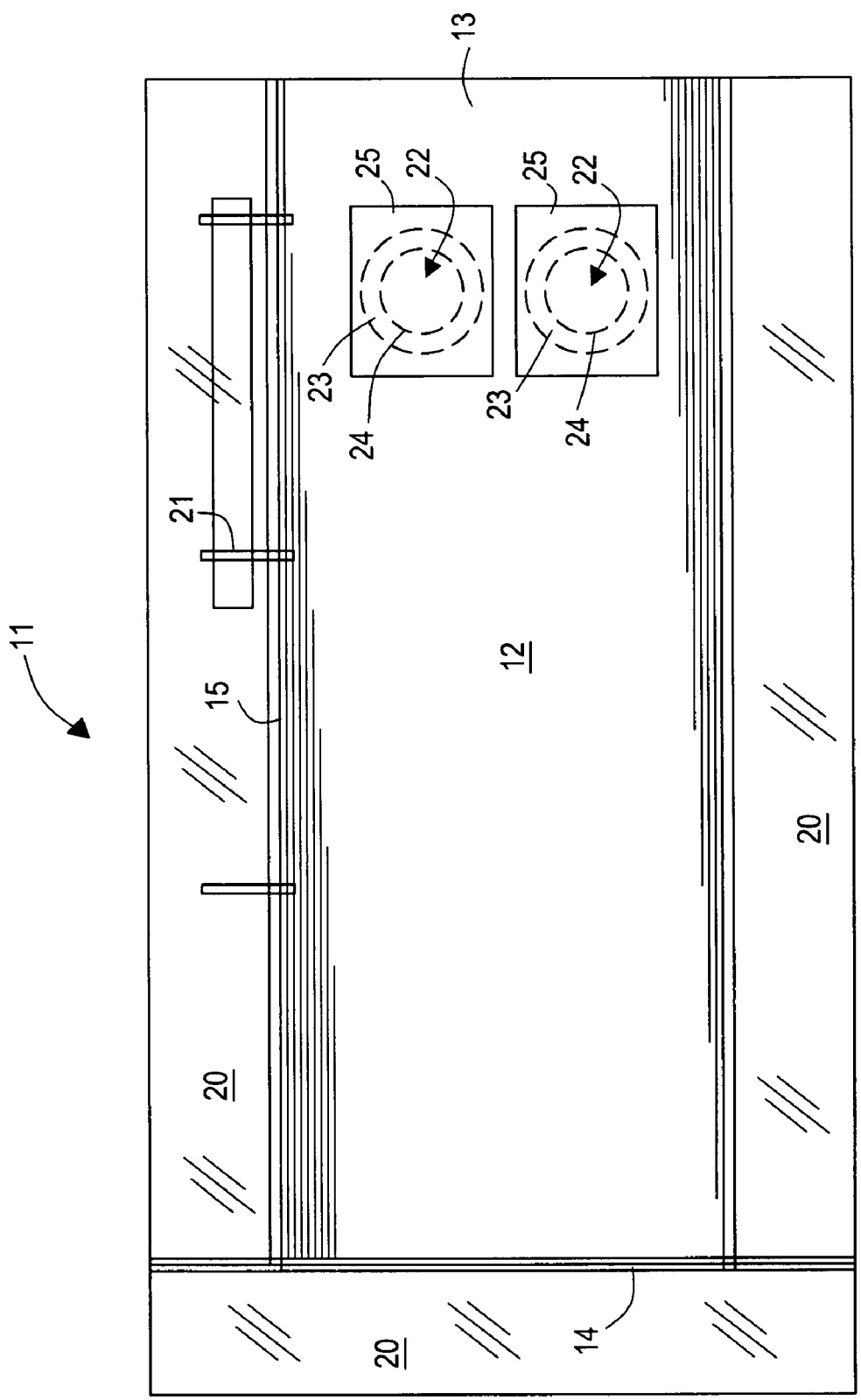
FIG. 1 is a bottom plan view of a prior art surgical drape.

Referring as a first matter to FIG. 1, a prior art, commercially available angiography drape 11 is shown. Prior art drape 11 includes main body 12, which is typically fabricated, at least in part, from a cellulosic substantially opaque material. Main body 12 has a first end 13, which is typically oriented towards the head of a patient, and an opposite second end 14, which is positioned near the feet of the patient. Main body 12 is defined by a peripheral edge 15. A transparent pliable perimeter portion 20 is provided, which is attached to peripheral edge 15. Perimeter portion 20 includes a plurality of deformable attachment members 21, which are adhesively affixed to the pliable perimeter portion 20 and which can be deformed in order to secure perimeter portion 20 to an adjacent object such as an examination table. Deformable attachment members 21 are bent or otherwise deformed in order to attach perimeter portion 20 to the object, thereby securing drape 11 in an orientation such that it is secured out of the way of the clinician and other healthcare workers working adjacent thereto.

Main body 12 includes a pair of windows, apertures or fenestrations 22, which are formed in predetermined positions near first end 13, and which provide a convenient location whereby a clinician may gain access to a patient's body positioned below surgical drape 11 in order to perform medical procedures. As should be understood, windows, apertures or fenestrations 22 formed in main body 12 are occluded, in part, by a flexible transparent adhesive border 23, which is affixed to main body 12 and which defines an aperture 24 through which the clinician will gain access to the patient's body. A release paper of conventional design 25 is releasably positioned in covering relation relative to flexible transparent adhesive border 23. Release paper 25 is removable, thereby exposing adhesive border 23 therebelow. Thereafter, the clinician positions aperture 24 in an appropriate orientation and flexible transparent adhesive border 23 secures main body 12 in place such that it does not move during the medical procedure.

Prior art drape 11 enables a clinician to perform a medical procedure on a patient's body through aperture 24, while providing a barrier between the treatment site (i.e., the portion of the patient's body being operated on) and the rest of the patient's body (i.e., the portion of the patient's body under drape 11). However, once the medical procedure is completed, the treatment site is susceptible to contamination due to exposure following the medical procedure. The coverings and drapes of the present invention address this shortcoming in prior art drape 11.

I. Coverings and Operating Room Drapes Containing the Same

The coverings and operating room drapes of the present invention may be provided in a variety of product configurations. Further, the coverings and operating room drapes of the present invention may comprise a variety of components, which provide one or more features to the coverings and operating room drapes.

A. Exemplary Covering and Drape Configurations

Figure 2:
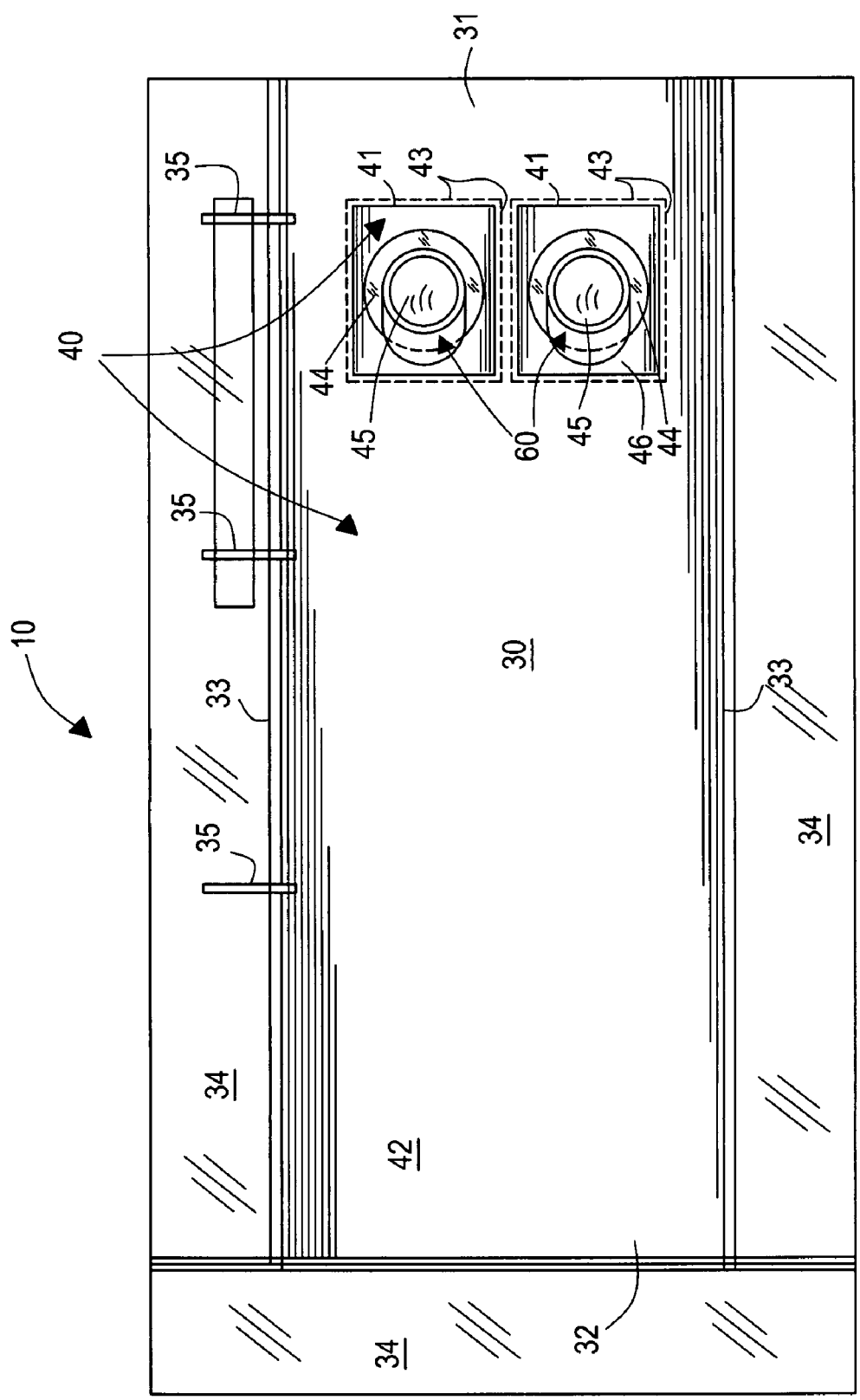
FIG. 2 is a top plan view of the covering for an aseptic treatment site of the present invention.

One exemplary covering configuration of the present invention is shown in FIGS. 2-6. Referring now to exemplary covering 10 as shown in FIG. 2, exemplary covering 10 is suitable for covering an aseptic treatment site. As shown in FIG. 2, exemplary covering 10 includes a main body 30 which may be fabricated, at least in part, from a cellulosic substrate which is substantially opaque. The main body 30 provides an aseptic barrier and is also capable of absorbing body or other fluids, which might be generated during a surgical or other medical procedure. The main body 30 has a first end 31 which is typically oriented at the head of the patient, (not shown) and a second end 32 which is oriented typically at or toward the feet of a patient. The main body 30 is defined by a peripheral edge 33. Similar to prior art drape 11 shown in FIG. 1, a transparent pliable perimeter portion 34 is provided. This perimeter portion also includes a deformable attachment members 35 which operate in a fashion similar to that described with respect to the prior art device shown in FIG. 1.

Figure 6:
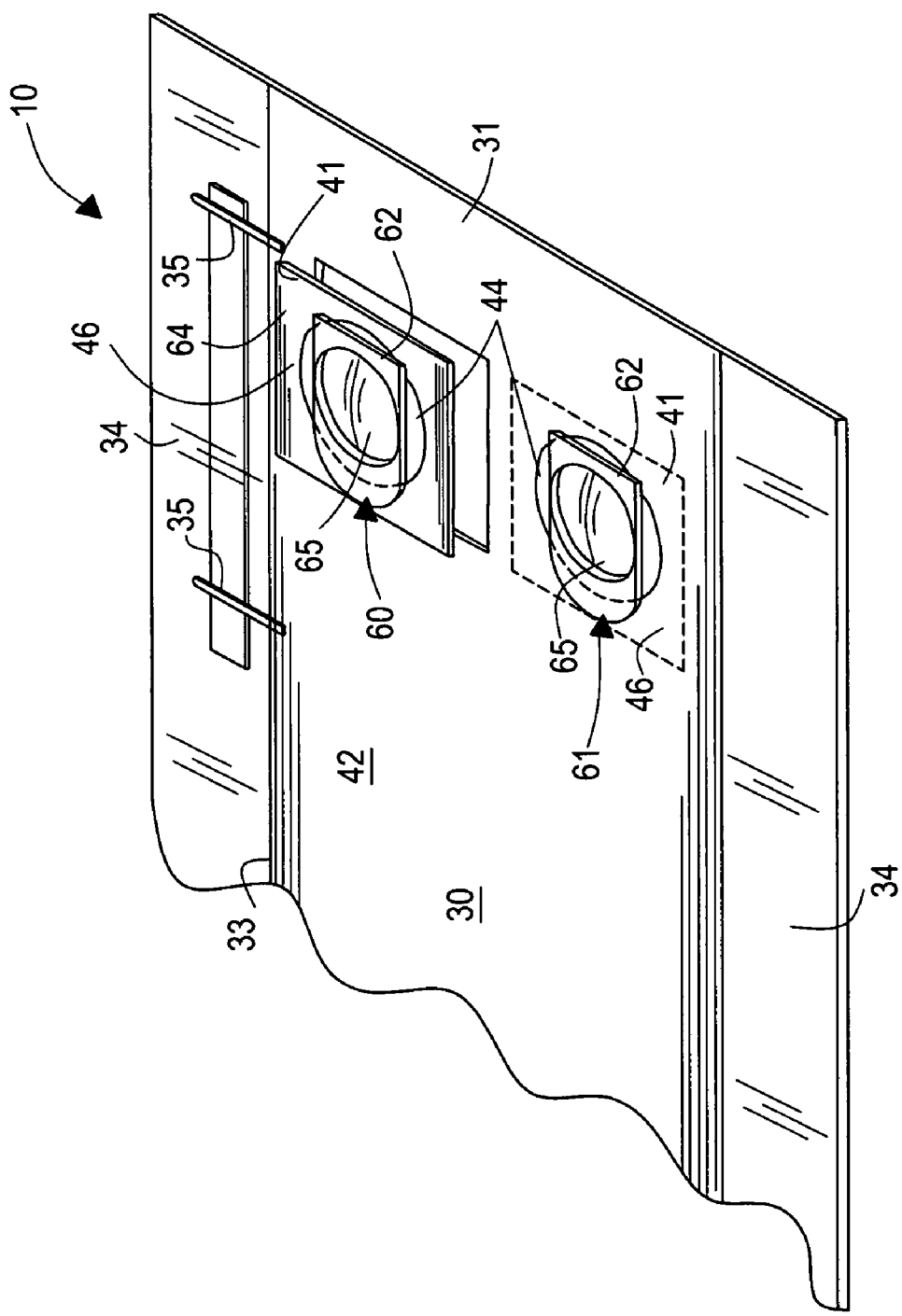
FIG. 6 is a fragmentary, perspective, view of the covering for an aseptic treatment site with one portion detached.

Referring still to FIGS. 2 and 6, exemplary covering 10 includes a pair of regions generally indicated by the numeral 40. The pair of regions includes a first region 41 and a selectively detachable second region 42 which is joined to the first region. As shown in FIG. 2, selectively detachable second region 42 comprises a preponderance of the main body 30. A plurality of perforations or weakened areas 43 are formed in a pattern in second region 42 and which surround, at least in part, first region 41. As will be appreciated from the discussion which follows, this plurality of weakened areas 43, which define a periphery of first region 41 permits second region 42 to be removed from first region 41 by tearing the main body 30 along perorations 43. First region 41 includes a first portion 44 which defines an aperture 45; and a second portion 46 which is made integral with first portion 44. As shown in FIG. 2, second region 42 is selectively detachable relative to second portion 46. As should be understood, second region 42 and second portion 46 may be fabricated from the same material or from different materials as desired. Yet further, first and second portions 44 and 46 may be fabricated from the same materials or from different materials depending upon the construction and end use of the same.

Figure 3:
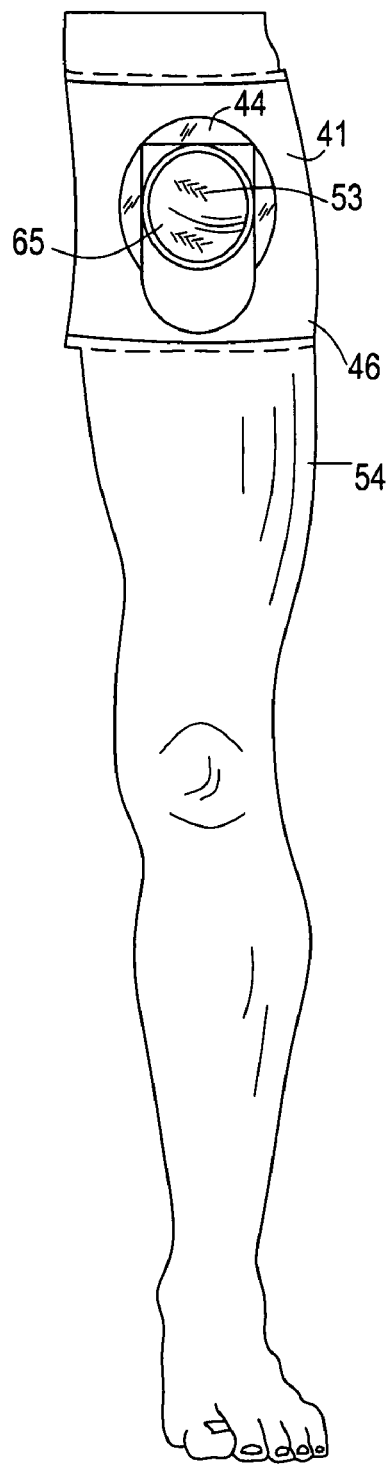
FIG. 3 is a partial, fragmentary top plan view of the covering for an aseptic treatment shown positioned on a patient's limb.
Figure 4:
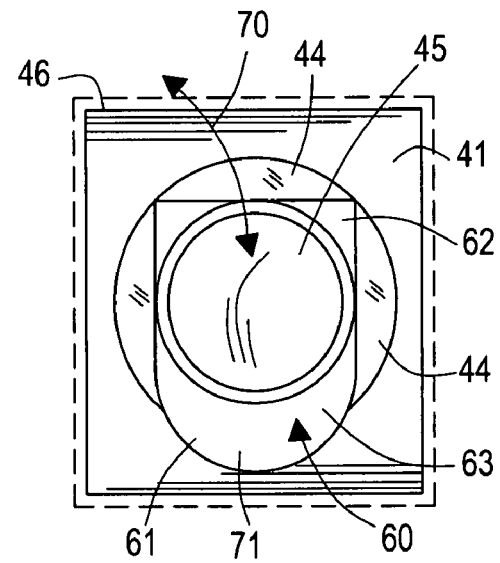
FIG. 4 is a fragmentary, somewhat enlarged, top plan view of the covering for an aseptic treatment site with a transparent cover shown in a covered position.
Figure 5:
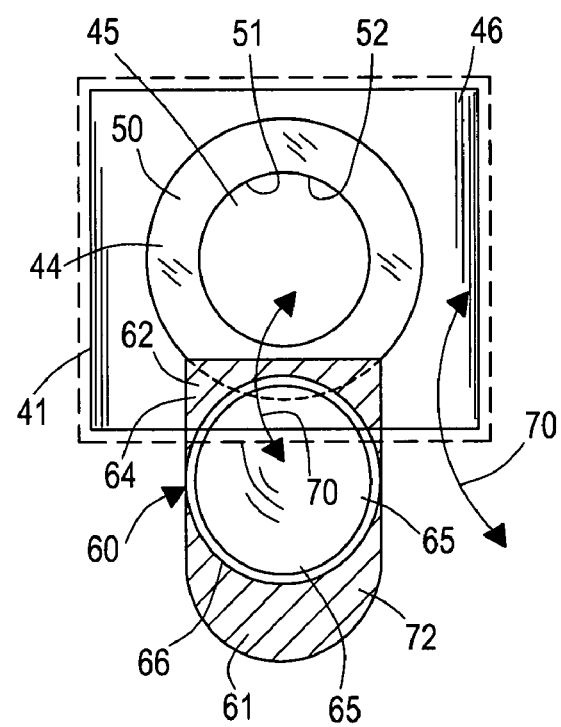
FIG. 5 is a fragmentary, top plan view of the covering for an aseptic treatment site with a transparent cover mounted on same shown in an uncovered position.

First portion 44 which defines aperture 45 has a first surface 50 and an opposite second surface 51 (shown in FIG. 5). Second surface 51 has an adhesive coating 52 applied thereto. Adhesive coating 52 is operable to adhere first portion 44 to a patient's body and in a given position such that it surrounds a surgical or medical intervention site 53 as shown in FIG. 3. Adhesive coating 52 has a predetermined adhesive strength. Surgical intervention site 53 may be on a limb 54 as shown in FIG. 3, on the torso of a patient (not shown), or any other body part of the patient. As shown in FIG. 2, exemplary covering 10 includes a transparent cover 60 which is moveably borne by first portion 44, and which is removably affixed in a substantially aseptic covering relation relative to aperture 45 (as shown in FIGS. 3 and 4). In particular, it can be seen in FIGS. 4 and 5 that transparent cover 60 is hingedly mounted on first portion 44. Transparent cover 60 has a first end 61 which may be grasped by a clinician, and an opposite second end 62 which is hingedly mounted to first portion 44. Still further, transparent cover 60 includes a first surface 63 and an opposite second surface 64. Transparent cover 60 defines a cavity 65 which, when transparent cover 60 is placed in an appropriate orientation in covering relation relative to aperture 45, ensures that transparent cover 60 does not directly contact surgical intervention site 53. Exemplary transparent cover 60 as shown in FIG. 3 permits a clinician to continuously view surgical intervention site 53 while maintaining surgical intervention site 53 in an aseptic condition. An adhesive layer 66 is provided, and which is applied in a given pattern on the second surface 64. This adhesive layer 66 is operable to adhesively attach transparent cover 60 in a covering relation relative to aperture 45 by adhering transparent cover 60 to an area of first portion 44 which is adjacent to aperture 45. This adhesive layer 66 has adhesive strength which is less than the adhesive strength provided by adhesive coating 52. This permits transparent cover 60 to be repeatedly moved between first and second positions 71 and 72 without pulling first portion 44 away from aseptic treatment site 53. Transparent cover 60 is moveable along a substantially arcuately path of travel indicated by path 70. Path of travel 70 is defined between first position 71 wherein transparent cover 60 is disposed in a substantially covering relation relative to aperture 45 (shown in FIG. 4), and second position 72 wherein transparent cover 60 allows access to aseptic treatment site 53.

In a further exemplary configuration of the present invention, the covering and/or drape comprises a cover assembly that can be used to cover an aseptic treatment site. In this embodiment, the drape comprises a cover assembly on a first location of the drape, wherein portions of the cover assembly may be used to cover and protect an aseptic treatment site on a patient. One such exemplary drape is depicted in FIG. 7.

Figure 7:
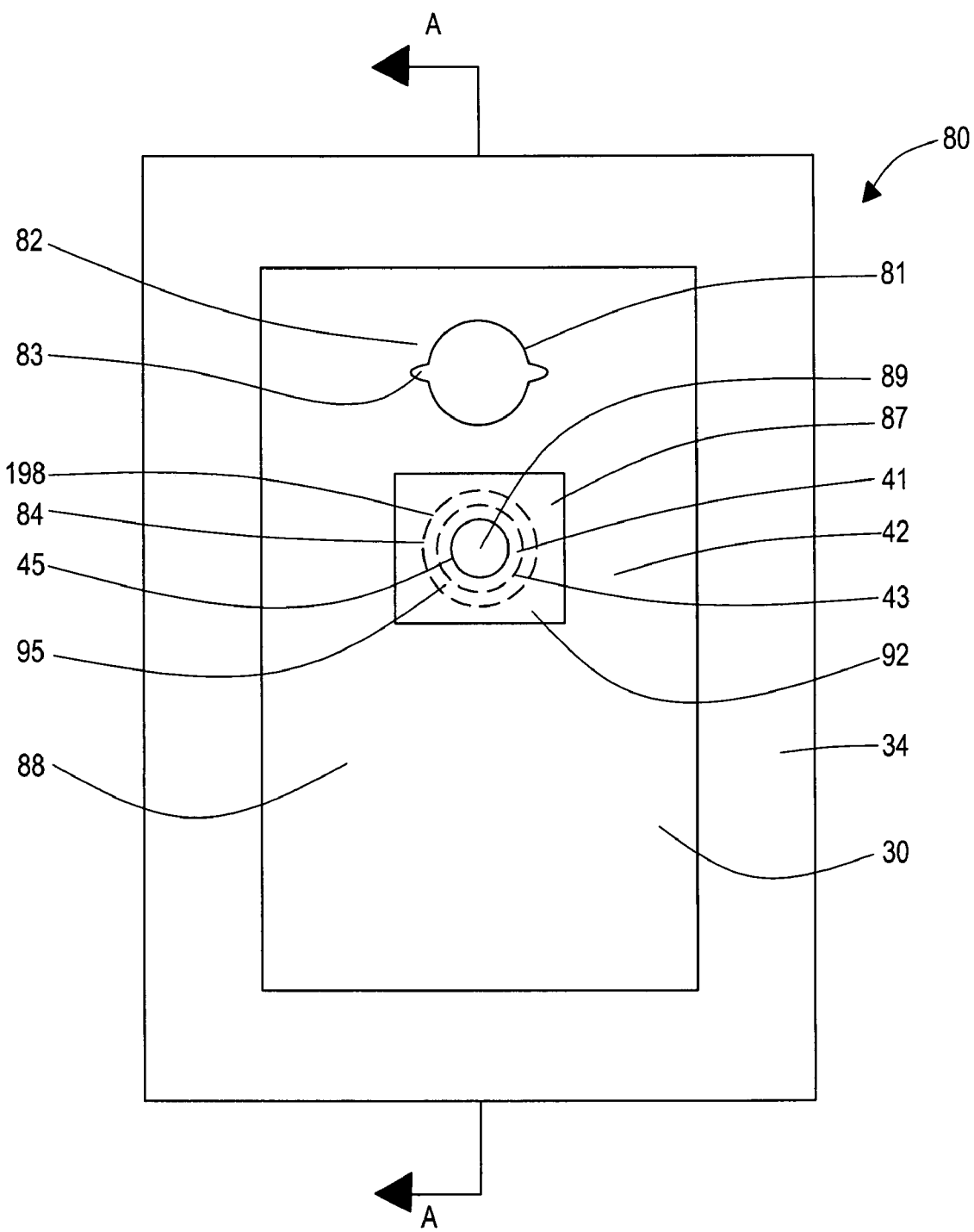
FIG. 7 depicts a top view of an exemplary drape of the present invention, wherein the drape comprises an exemplary cover assembly.

As shown in FIG. 7, exemplary drape 80 comprises main body 30 and perimeter portion 34 surrounding main body 30. It should be noted that perimeter portion 34 does not necessarily have to extend along the complete perimeter of main body 30. For example, perimeter portion 34 may only be present along opposite edges of main body 30 (see, for example, exemplary drape 100 in FIG. 10) or along three sides of main body 30 (see, for example, exemplary covering 10 in FIG. 2). Exemplary drape 80 further comprises (i) fenestration 84 having fenestration area 95 bound by outermost circular dashed line 198; (ii) adhesive film 87 on an upper surface 88 of main body 30, wherein adhesive film 87 has a non-tacky upper surface 92 (shown in FIG. 7) and a tacky, adhesive surface 93 on a lower side (shown in FIG. 8); (iii) aperture 45 within adhesive sheet 87; and (iv) cover assembly 81 at first location 82 on upper surface 88 of main body 30. At least a portion of adhesive film 87 extends over a portion of fenestration area 95. Adhesive film 87 comprises an adhesive film fenestration or aperture 45 having adhesive film fenestration area 89. Adhesive film 87 is releasably attachable to a portion of a patient's body proximate an area that is to be operated on. The area to be operated on may be examined through adhesive film fenestration or aperture 45.

Like exemplary covering 10 shown in FIGS. 2 and 6, exemplary drape 80 shown in FIG. 7 comprises first region 41 and second region 42. First region 41 and second region 42 may be detached from one another along plurality of perforations or weakened areas 43. As shown in FIG. 7, plurality of perforations or weakened areas 43 form a circular pattern positioned a minimal distance, $d_m$, from edges of aperture 45. As discussed previously with regard to exemplary covering 10 and further discussed below, once an aseptic treatment site has been covered and protected, first region 41 can be detached from second region 42 to remain on a patient's body, and maintain the aseptic treatment site in an aseptic condition.

Depending on a number of factors including, but not limited to, the size of aperture 45, the adhesive strength of adhesive film 87, the size of the aseptic treatment site, and the location of the aseptic treatment site on a patient, minimal distance, $d_m$, can vary as desired. Typically, minimal distance, $d_m$, is at least about 1.0 cm, and up to about 10.0 cm in length; however, there is no limitation on the length of minimal distance, $d_m$. Further, although plurality of perforations or weakened areas 43 is shown as being within adhesive film 87, it should be understood that plurality of perforations or weakened areas 43 can extend through adhesive film 87 alone, main body 30 alone, or adhesive film 87 in combination with main body 30 depending on the desired size of first region 41. Even further, although aperture 45, fenestration 84 and the pattern of plurality of perforations or weakened areas 43 are shown as having a circular configuration, it should be noted that each of aperture 45, fenestration 84 and the pattern of plurality of perforations or weakened areas 43 may independently have any geometric shape including, but not limited to, circular, square, rectangular, triangular, etc.

Figure 8:
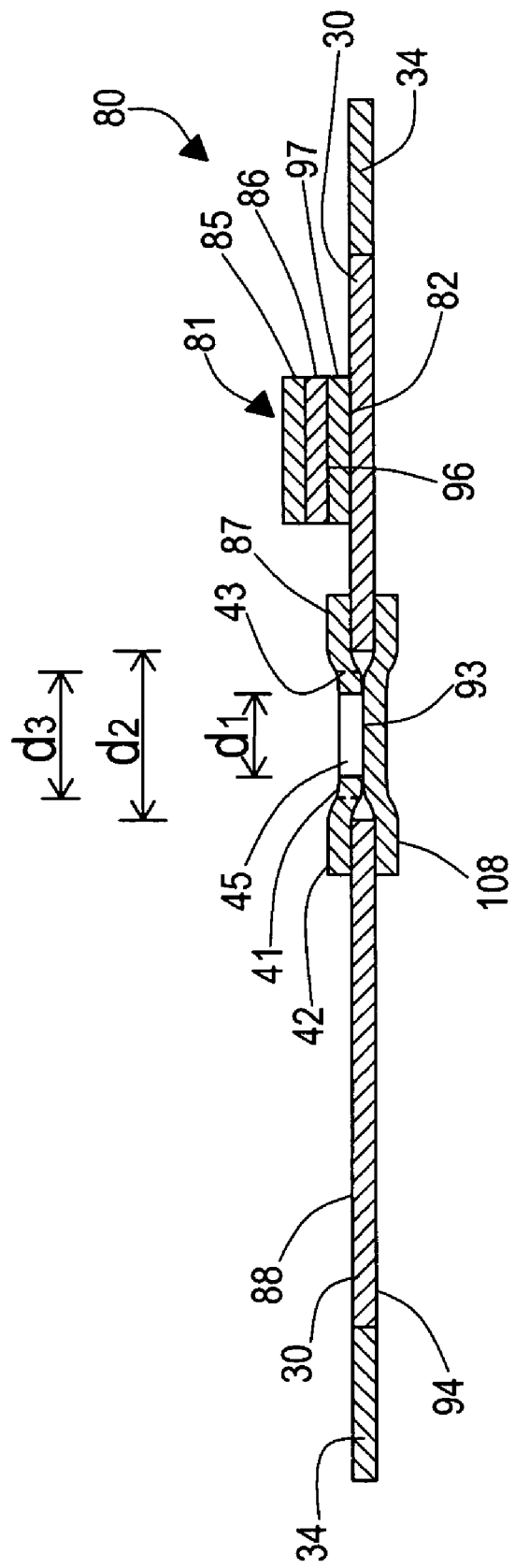
FIG. 8 depicts a cross-sectional view of the exemplary drape of FIG. 7 along line A-A shown in FIG. 7.

A cross-sectional view of exemplary drape 80 viewed along line A-A of FIG. 7 is provided in FIG. 8. As shown in FIG. 8, exemplary drape 80 comprises an uppermost adhesive film 87 positioned on upper surface 88 of main body 30. Adhesive film 87 has adhesive film fenestration or aperture 45 having a cross-sectional dimension, $d_1$. Main body 30 comprises fenestration 84 having a cross-sectional dimension, $d_2$, wherein $d_2$ has a greater length than $d_1$. This enables at least a portion of adhesive film 87 to extend over fenestration area 95. Further, in this exemplary embodiment, a pattern of a plurality of perforations or weakened areas 43 has a cross-sectional dimension, $d_3$, wherein $d_3$ has a length greater than $d_1$ and a length less than $d_2$. In other embodiments, $d_3$ may have a length equal to or greater than the length of $d_2$.

As shown in FIG. 8, prior to actual use, exemplary drape 80 comprises drape release liner 108, which provides temporary protection to adhesive surface 93 of adhesive film 87. Drape release liner 108 is adjacent to lower surface 94 of main body 30, and releasably adhered to portions of adhesive film 87 that extend over fenestration area 95. Further, as shown in FIG. 8, cover assembly 81 may comprise one or more separate components. In this exemplary embodiment, cover assembly 81 comprises (i) a first release liner 85 having one or more optional tabs or extensions 83 suitable for gripping first release liner 85; (ii) a transparent cover 86 having a transparent cover outer periphery and being releasably attached to first release liner 85, wherein transparent cover 86 has an adhesive layer 96 on a lower surface of transparent cover 86 opposite first release liner 85; and (iii) a second release liner 97 attached to first location 82 of drape 80. It should be noted that in other embodiments of the present invention, second release liner 97 may not be necessary. For example, in an alternative embodiment, first location 82 of drape 80 may be treated with a release coating or may be manufactured from drape material having release properties such that adhesive layer 96 of transparent cover 86 releasably attaches directly to first location 82 of drape 80.

Cover assembly 81 and its components may have any desired size and shape. Like aperture 45, fenestration 84 and the pattern of plurality of perforations or weakened areas 43 described above, cover assembly 81 and its components may each independently have any geometric shape including, but not limited to, circular, square, rectangular, triangular, etc. Typically, transparent cover 86 has a shape similar to aperture 45 (e.g., a circular configuration as shown in FIG. 7), and a size such that transparent cover 86 completely covers aperture 45 and extends over a portion of adhesive film 87 (see, for example, FIG. 9B). Desirably, transparent cover 86 completely covers aperture 45 and extends a distance, $d_e$, over a portion of adhesive film 87, wherein $d_e$ is greater than 1.0 cm and up to a length such that transparent cover 86 abuts weakened areas 43 (i.e., transparent cover 86 covers all of first region 41).

Cover assembly 81 may be positioned at any first location 82 of drape 80, wherein first location 82 is any location on drape 80. Typically, first location 82 is on upper surface 88 of main body 30; however, first location 82 could be in any other possible location, such as on perimeter portion 34. In one exemplary embodiment, first location 82 is an area proximate to a fenestration in the drape. In this exemplary embodiment, a portion of transparent cover 86 may be attached to first location 82 such that the step of removing first release liner 85 and adhesively bonding transparent cover 86 to second location on the drape to surround the aseptic treatment site on the patient requires minimal effort on the part of a user. Such an exemplary embodiment is shown in FIG. 10.

Figure 10:
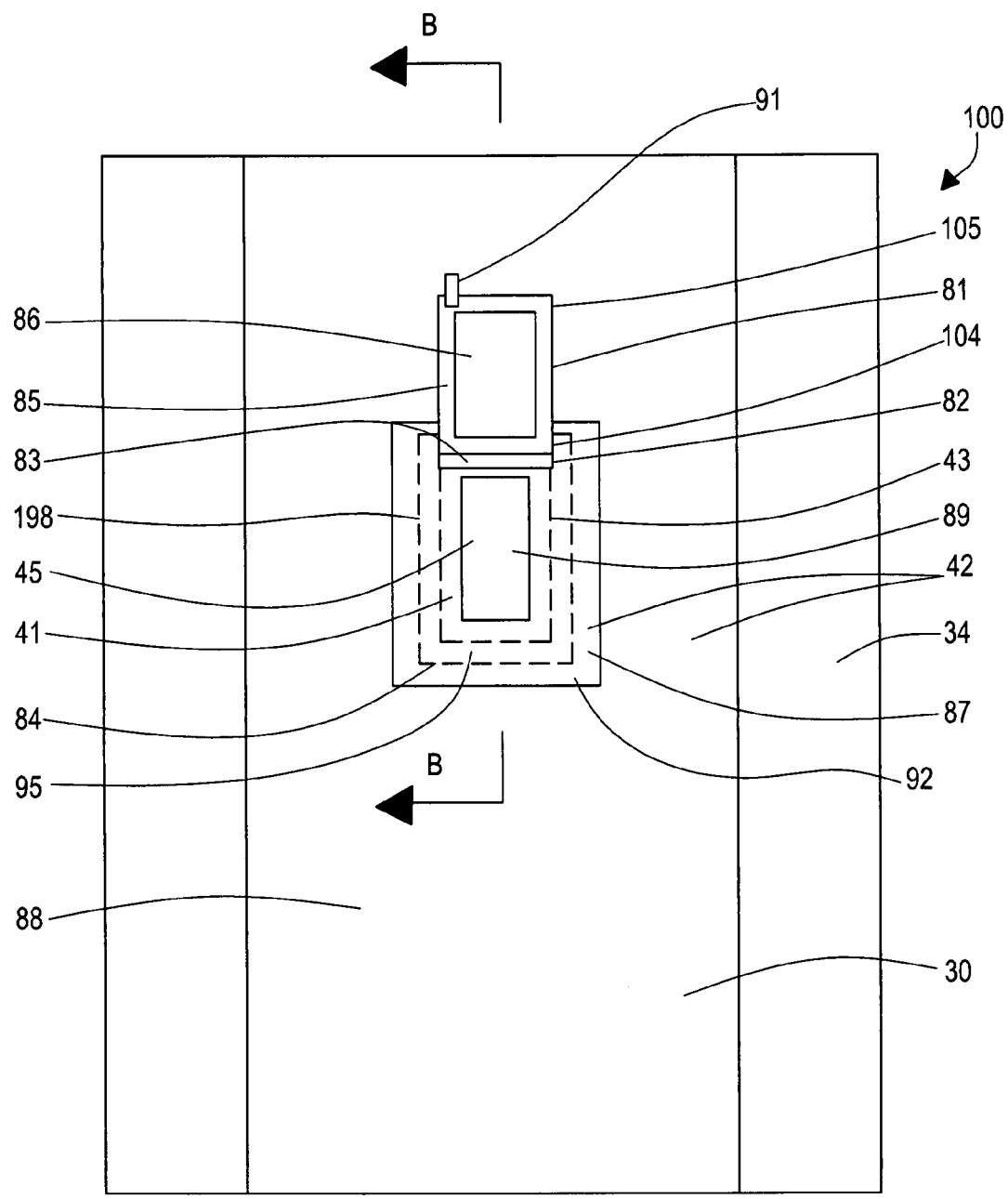
FIG. 10 depicts a top view of another exemplary drape of the present invention, wherein the drape comprises another exemplary cover assembly.

As shown in FIG. 10, exemplary drape 100 comprises main body 30 and perimeter portion 34 extending along opposite edges of main body 30. Exemplary drape 100 further comprises (i) fenestration 84 having fenestration area 95 bound by outermost circular dashed line 198; (ii) adhesive film 87 on an upper surface 88 of main body 30, wherein adhesive film 87 has a non-tacky upper surface 92 and a tacky, adhesive surface 93 on a lower side (shown in FIG. 12A); (iii) aperture 45 within adhesive sheet 87; and (iv) cover assembly 81 at first location 82 on upper surface 88 of main body 30. At least a portion of adhesive film 87 extends over a portion of fenestration area 95. Adhesive film 87 comprises an adhesive film fenestration or aperture 45 having adhesive film fenestration area 89. Adhesive film 87 is releasably attachable to a portion of a patient's body proximate an area that is to be operated on. The area to be operated on may be examined through adhesive film fenestration or aperture 45 as discussed above.

Like exemplary covering 10 shown in FIGS. 2 and 6 and exemplary drape 80 shown in FIG. 7, exemplary drape 100 shown in FIG. 10 comprises first region 41 and second region 42 separated and detachable from one another along plurality of perforations or weakened areas 43. As shown in FIG. 10, plurality of perforations or weakened areas 43 form a rectangular pattern positioned a minimal distance, $d_m$, from edges of aperture 45. As discussed previously with regard to exemplary covering 10 and exemplary drape 80, once an aseptic treatment site has been covered and protected, first region 41 can be detached from second region 42 to remain on a patient's body, and maintain the aseptic treatment site in an aseptic condition.

Cover assembly 81 in this embodiment comprises (i) a first release liner 85 having one or more optional tabs or extensions 83 suitable for gripping first release liner 85; and (ii) a transparent cover 86 having a transparent cover outer periphery and being releasably attached to first release liner 85, wherein transparent cover 86 has an adhesive layer 96 on an upper surface of transparent cover 86 adjacent to first release liner 85. A portion of adhesive layer 96 of transparent cover 86 is bonded to drape 100 at first location 82, which is positioned proximate aperture 45. In this exemplary embodiment, first location 82 is within first region 41, which is bound by plurality of perforations or weakened areas 43. Further, a piece of tape 91 is used to temporarily secure unattached end 105 of cover assembly 81 to upper surface 88 of exemplary drape 100 prior to use.

Figure 11:
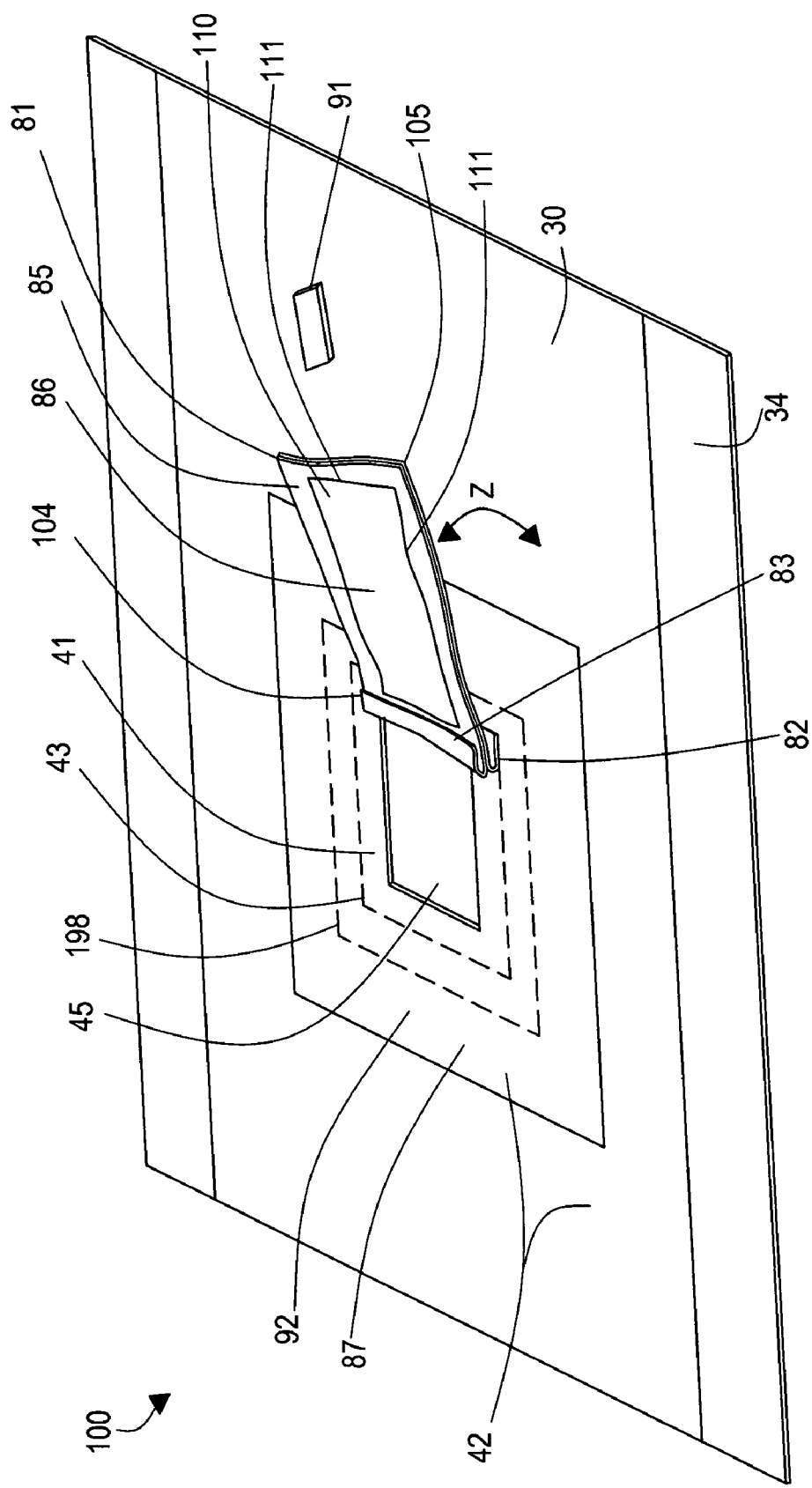
FIG. 11 depicts a side view of the exemplary drape of FIG. 10.

Another view of exemplary drape 100 is provided in FIG. 11. As shown in FIG. 11, attached end 104 of cover assembly 81 is attached to drape 100 at first location 82. Unattached end 105 of cover assembly 81 may move away from upper surface 88 of exemplary drape 100 along arrow Z when detached from piece of tape 91. Tab 83 of first release liner 85 extends from first location 82 to provide a gripping surface for a user (as described in more detail below).

Figure 12A:
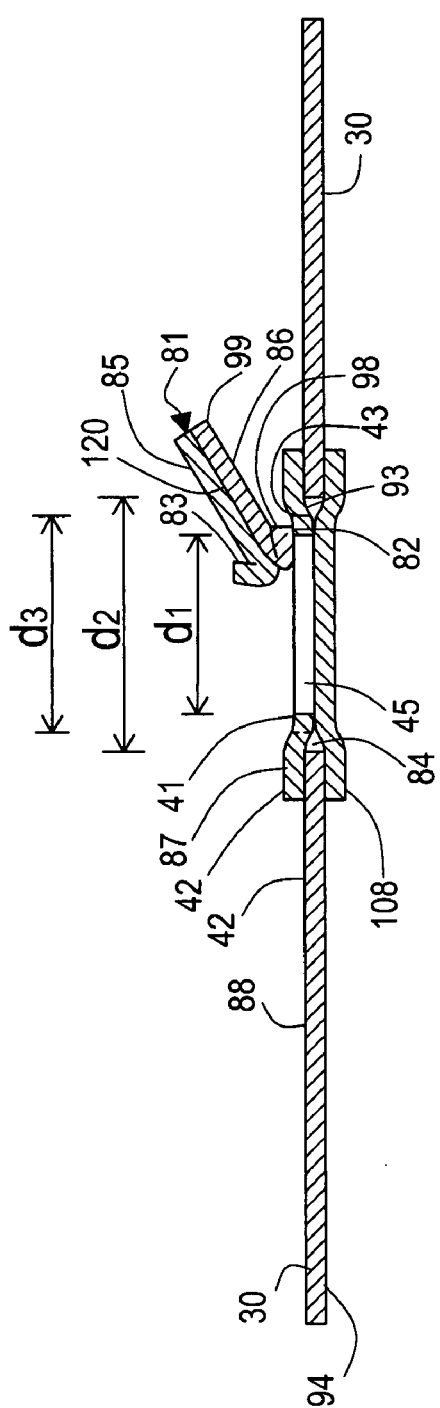

A cross-sectional view of exemplary drape 100 viewed along line B-B of FIG. 10 is provided in FIG. 12A. As shown in FIG. 12A, exemplary drape 100 comprises an uppermost adhesive film 87 positioned on upper surface 88 of main body 30. Adhesive film 87 has adhesive film fenestration or aperture 45 having a cross-sectional dimension, $d_1$. Main body 30 comprises fenestration 84 having a cross-sectional dimension, $d_2$, wherein $d_2$ has a greater length than $d_1$. This enables at least a portion of adhesive film 87 to extend over fenestration area 95. Further, in this exemplary embodiment, pattern of plurality of perforations or weakened areas 43 has a cross-sectional dimension, $d_3$, wherein $d_3$ has a length greater than $d_1$ and less than $d_2$. As discussed above, in other embodiments, $d_3$ may have a length equal to or greater than a length of $d_2$.

As shown in FIG. 12A, prior to actual use, exemplary drape 100 comprises drape release liner 108, which provides temporary protection to adhesive surface 93 of adhesive film 87. Drape release liner 108 is adjacent to lower surface 94 of main body 30, and releasably adhered to portions of adhesive film 87 that extend over fenestration area 95. Further, as shown in FIG. 12A, cover assembly 81 is attached to first location 82 via a portion of adhesive layer 96 on transparent cover 86.

B. Covering and Operating Room Drape Components

As described above, the coverings and operating room drapes of the present invention may comprise a number of components. A description of some of the suitable exemplary components is provided below. The coverings and operating room drapes of the present invention may comprise, but are not limited to, one or more of the following components.

1. Main Body

The disposable operating room drapes of the present invention comprises a main body such as exemplary main body 30 of exemplary disposable operating room covering/drapes 10, 80 and 100 shown in FIGS. 2, 7 and 10 respectively. The main body of the operating room covering/drapes of the present invention may comprise one or more layers of material bonded to one another. Suitable layers include, but are not limited to, film layers; fabric layers such as woven, nonwoven and knitted fabric layers; foam layers; and combinations thereof.

In one desired embodiment of the present invention, the main body comprises a multi-layer article comprising a lower liquid impervious layer (i.e., a layer that forms lower surface 94 of main body 30), and an upper fiber-containing layer (i.e., a layer that forms upper surface 88 of main body 30) adjacent to the liquid impervious layer. Desirably, the upper fiber-containing layer possesses some degree of liquid absorbency. The liquid impervious layer may comprise a polymeric film-forming material, such as polyethylene, and typically has an average layer thickness of less than about 50 microns (µm) (about 2 mil). Desirably, the polymeric film-forming material comprises a material having a relatively high coefficient of friction or degree of tackiness so that the main body does not slip off of an operating room table or table mattress during use. One desired polymeric film-forming material having a relatively high coefficient of friction comprises polyethylene.

In a further desired embodiment of the present invention, the main body comprises a single-layer article comprising a single fiber-containing layer. Desirably, as in the two-layered construction described above, the fiber-containing layer possesses some degree of liquid absorbency.

In either of the above desired embodiments, the fiber-containing layer may comprise a woven or nonwoven fabric layer, or may comprise a layer of fibers adjacent to a liquid impervious layer. The fibers of the fiber-containing layer may comprise naturally occurring fibers (e.g., cellulosic fibers, pulp fibers, etc.), polymeric fibers (e.g., polypropylene fibers), or a combination thereof. Suitable polymeric film-forming materials include, but are not limited to, polypropylene, polyamide, and polyester. The fiber-containing layer typically has an average layer thickness of less than about 250 microns (µm) (about 10 mil). In one desired embodiment of the present invention, the fiber-containing layer comprises a polypropylene spunbonded fabric layer having a basis weight of about 33.9 grams per square meter (gsm) (about 1 ounce per square yard).

Although a single-layer or two-layered construction, as described above, may be used in the present invention, in other embodiments, a three or four layered construction may be used wherein at least one layer containing superabsorbent material or particles (SAP) is interposed between the above-described liquid impervious layer and the above-described fiber-containing layer or between two fiber-containing layers. The SAP-containing layer or layers may further comprise additional components such as fibrous materials (e.g., pulp fibers, synthetic fibers, or a combination thereof), filler materials, or a combination thereof.

The SAP-containing layer or layers may each comprise a substantially uniform distribution of superabsorbent material or particles across an area of the main body, or alternatively, may comprise a non-uniform distribution of superabsorbent material or particles across an area of the main body. For example, a main body useful in the present invention may have a layer of superabsorbent material or particles within a central location of the main body (e.g., an area positioned directly above a central location of an operating room table or table mattress), but be substantially free of superabsorbent material or particles in an outer periphery of the main body.

Any known superabsorbent material may be used in the main body of the present invention. Suitable commercially available superabsorbent materials include, but are not limited to, superabsorbent materials available from Stockhausen (Greensboro, N.C.) and Dow Chemical (Midland, Mich.).

Operating room drapes used in the present invention typically have dimensions so that the operating room drape may completely cover an upper surface of an operating room table or table mattress. In one exemplary embodiment of the present invention, the main body of the operating room drape has a width ranging from about 61.0 centimeters (cm) (24 inches (in)) to about 241.3 cm (95 in), and a length ranging from about 101.6 cm (40 in) to about 381 cm (150 in). In one desired embodiment, the main body of the operating room drape has a width of about 190.5 cm (75 in), and a length of about 317.5 cm (125 in).

As shown in FIGS. 2, 7 and 10, main body 30 comprises at least one fenestration 84. Fenestration 84 has a fenestration area 95 that may vary in size depending on a number of factors including, but not limited to, the final use of the operating room drape. Fenestration 84 typically has one or more dimensions (i.e., length, width or diameter), wherein each dimension is less than about 61.0 cm (24 in). Typically, fenestration 84 has one or more dimensions, wherein each dimension ranges from about 15.2 cm (6.0 in) to about 45.7 cm (18 in), and more desirably, ranges from about 20.3 cm (8 in) to about 30.5 cm (12 in).

Although not shown in FIGS. 7 and 10, it should be understood that main body 30 may comprise two or more separate fenestrations 84 positioned along any portion of upper surface 88 of main body 30. When main body 30 comprises more than one fenestration 84, each fenestration 84 may have similar or different dimensions and/or shapes.

2. Adhesive Film

The operating room coverings/drapes of the present invention also comprise an adhesive film such as exemplary adhesive film 87 of exemplary operating room drapes 80 and 100 shown in FIGS. 7 and 10 respectively. The adhesive film is adhesively bonded to an upper surface of the main body. The upper surface of the adhesive film typically has very little or no tackiness, while the lower surface (i.e., the surface next to the main body) has an adhesive thereon. A typical construction of the adhesive film comprises an upper backing layer, such as a polymer film, and a lower pressure sensitive adhesive layer on the backing layer. Any polymer film backing layer and any pressure sensitive adhesive may be used in the present invention. In one exemplary embodiment of the present invention, the adhesive film comprises a polyethylene or polyester backing and a pressure sensitive adhesive comprising poly(meth)acrylate; diene rubber such as natural rubber, polyisoprene, and polybutadiene; thermoplastic elastomer; block copolymers such as styrene-isoprene and styrene-isoprene-styrene (SIS) block copolymers, ethylene-propylene-diene polymers, and styrene-butadiene polymers; poly-alpha-olefin; amorphous polyolefin; ethylene-containing copolymer such as ethylene vinyl acetate, ethylacrylate, and ethyl methacrylate; polyurethane; polyamide; epoxy; polyesters; and combinations thereof.

In one desired embodiment, the adhesive film completely surrounds the fenestration (e.g., fenestration 84) and fenestration area (e.g., fenestration area 95) and comprises an adhesive film fenestration (e.g., aperture 45), wherein an outermost edge of the adhesive film fenestration is positioned within the fenestration area such that a portion of the adhesive film extends along and completely surrounds an outer edge of the fenestration area. Such a configuration is shown in FIGS. 2, 7 and 10. Desirably, the outermost edge of adhesive film fenestration (e.g., aperture 45) (i) is positioned completely within the fenestration area (e.g., fenestration area 95), and (ii) extends from about 12.6 millimeters (mm) (0.5 in) to about 50.8 mm (2.0 in) into fenestration area (e.g., fenestration area 95) from any edge of the main body fenestration (e.g., fenestration 84).

As discussed above, the fenestration and the adhesive film fenestration (e.g., aperture 45) may have any desired shape including, but not limited to, a circular shape, a rectangular shape, a square shape, a triangular shape, an octagonal shape, etc. Desirably, the fenestration (e.g., fenestration 84) has a first opening shape, and the adhesive film fenestration (e.g., aperture 45) has an adhesive film opening shape substantially similar to the first opening shape. For example, the first opening shape and the adhesive film opening shape may each independently be a circular shape. In this embodiment, as discussed above, it is desirable for the fenestration area (e.g., fenestration area 95) to be greater than an adhesive film fenestration area (e.g., aperture 45) (i.e., the fenestration and the adhesive film fenestration or aperture have a circular shape, but the adhesive film fenestration or aperture circular area is smaller than the fenestration circular area such that the adhesive film fenestration circular area is positioned completely within the first fenestration area). In one desired embodiment of the present invention, the first fenestration and the adhesive film fenestration have a circular shape, but the adhesive film fenestration has a diameter of about 20.3 cm (8 in), while the first fenestration has a diameter of about 25.4 cm (10 in).

Although not shown in FIGS. 2, 7 and 10, it should be understood that adhesive film 87 may comprise two or more separate adhesive film fenestrations or apertures 45 positioned within adhesive film 87. When adhesive film 87 comprises more than one adhesive film fenestration 45, each adhesive film fenestration 45 may have similar or different dimensions and/or shapes. Desirably, each adhesive film fenestration 45 is aligned with a corresponding fenestration 84 so that outermost edges of each adhesive film fenestration 45 are positioned within fenestration areas 95 such that portions of adhesive film 87 extend along and completely surround outer edges of each of the fenestration areas 95. Further, in an alternative configuration not shown in FIGS. 2, 7 and 10, it should be understood that multiple adhesive films 87 may be present and aligned with multiple corresponding fenestrations 84.

3. Perimeter Portion

The operating room coverings/drapes of the present invention may also comprise a perimeter portion such as exemplary perimeter portion 34 of exemplary disposable operating room covering/drapes 10, 80 and 100 shown in FIGS. 2, 7 and 10 respectively. The perimeter portion is desirably joined to the above-described main body along at least a portion of an outer periphery of the main body. For example, as shown in FIGS. 7 and 10, exemplary perimeter portion 34 may be joined to main body 30 along two or more outer edges of main body 30.

Perimeter portion used in the present invention typically comprises a single-layer material such as a film layer, a paper layer, or a fabric layer. Desirably, the perimeter portion comprises a film material, more desirably, a transparent film material. The film material may comprise any polymeric film-forming material, such as polyethylene, and typically has an average layer thickness of less than about 50 microns (μm) (about 2 mil).

In a further embodiment, the perimeter portion is an extension of a liquid-impervious layer that extends below and is integrally attached to main body 30. In this embodiment, main body 30 has a two-layered construction as described above, while perimeter portions 34 comprises the same film-forming material used to form the lower layer of main body 30.

In yet a further embodiment, the perimeter portion is an extension of a liquid-pervious nonwoven fabric layer that extends below and is integrally attached to main body 30. In this embodiment, main body 30 has a two-layered construction as described above, while perimeter portion 34 comprises the same nonwoven fabric material used to form the lower layer of main body 30.

4. Release Liners

The operating room drapes of the present invention may further comprise a release liner such as exemplary release liners 108, 85 and 97 of exemplary disposable operating room drape 80 shown in FIG. 8. Each release liner may be any conventional material having release properties including, but not limited to, a polymeric film having release properties, a polymeric film having a separate release coating thereon, or a paper substrate having a release coating thereon. Further, each release liner may have any dimensions and shape as long as the release liner is able to cover (i) any exposed areas of adhesive film (i) extending over the fenestration area within the above-described main body, or (ii) any adhesive on the transparent cover of a given cover assembly.

Suitable release liners that may be used in the present invention include, but are not limited to, silicone coated papers, and silicone coated films, such as polyester films. Examples of suitable commercially available release liners include, but are not limited to, release liners sold under the trade designation AKROSIL™ available from Akrosil Europe (Huerlen, Netherlands) and International Paper (Menasha, Wis.); and release liners available from Daubert Coated Products, Inc. (Dixon, Ill.).

When adhesive film 87 comprises two or more separate adhesive film fenestrations 45 or when two or more adhesive films 87 are present, one or more release liners 108 may be used to temporarily cover any exposed areas of adhesive on a lower surface of adhesive film(s) 87.

5. Transparent Covers

The operating room drapes of the present invention may further comprise a transparent cover as a component of a cover assembly such as exemplary transparent cover 86 of exemplary disposable operating room drapes 80 and 100 shown in FIGS. 8 and 12A respectively. Typically, the transparent cover comprises a single-layer base material, such as a film layer, with an adhesive coating on at least a portion of an outer surface of the base material. The base material may comprise any polymeric film-forming or thermoformable material, such as polyurethane, polypropylene, polyethylene or ethylene copolymer. When the base material comprises a polymeric film, the base material typically has an average layer thickness of less than about 50 microns (μm) (about 2 mil).

In one desired embodiment of the present invention, the transparent cover comprises a polymer base film that is capable of being stretched at least about 5% (at least about 10%, at least about 15%, or at least about 25%) without breaking. Desirably, the stretchable polymer film comprises a polyurethane or an ethylene methyl acrylate copolymer.

The adhesive coating may comprise any of the above-described pressure sensitive adhesive materials. The adhesive coating may cover a portion of an outer surface of the base material or the entire outer surface. For example, in exemplary drape 80 shown in FIG. 8, adhesive layer 96 on a lower surface of transparent cover 86 may cover the entire lower surface of transparent cover 86 or less than the entire lower surface of transparent cover 86, for example, only a perimeter portion of the lower surface of transparent cover 86 such that a portion of the lower surface of transparent cover 86 does not adhere to the patient. Further, as shown in exemplary drape 100 in FIGS. 10, 11 and 12A, adhesive layer 96 on an outer surface of transparent cover 86 only covers an outer perimeter of the outer surface of transparent cover 86 covered by first release liner 85. In this embodiment, a portion of the outer surface of transparent cover 86 (designated in FIG. 11 as area 110, which is outlined by lines 111) does not adhere to the patient.

A number of commercially available materials may be used to form transparent cover 86. Suitable materials include, but are not limited to, adhesive films commercially available from The 3M Company (St. Paul, Minn.) under the trade designation 3M™ SINGLE COATED POLYURETHANE MEDICAL TAPES, such as Product Number 9842. This particular product comprising a 0.02 mm (0.8 mil) translucent polyurethane backing film and an acrylate pressure-sensitive adhesive layer on an outer surface of the backing film to form a polyurethane tape having a thickness of about 0.05 mm (1.8 mil).

6. Component Additives

Any of the above-described operating room covering/drape components may further comprise one or more additives coated onto or incorporated in one or more of the materials used to form the individual component. Suitable additives include, but are not limited to, antimicrobial agents, colorants, additives to increase the coefficient of friction of a given component layer, etc. In one desired embodiment of the present invention, one or more components of the operating room coverings/drapes comprise an antimicrobial agent incorporated therein. Suitable antimicrobial agents include, but are not limited to, triclosan and other antimicrobial agents commercially available under the trade designation MICROBAN®.

For example, one or more of adhesive film 87, main body 30, perimeter portion 34, and transparent cover 60 may contain one or more of the above-mentioned additives, such as antimicrobial agents commercially available under the trade designation MICROBAN®.

II. Methods of Making Operating Room Coverings/Drapes

The present invention is further directed to methods of making an operating room covering or drape. Any of the above-described individual components used to form the operating room covering or drape may be formed using conventional methods. For example, liquid impervious film layers may be forming via any film-forming process including, but not limited to, a film extrusion process, a film-blowing process, etc. Fiber-containing layers, such as a woven fabric layer or a nonwoven fabric layer, may be formed using conventional weaving or web-forming processes including, but not limited to, meltblowing processes, spunbonding processes, spunlacing processes, needle-punching processes, hydroentangling processes, etc.

Films and fabric layers may be joined to one another using any conventional bonding technique including, but not limited to, thermal bonding processes, adhesive bonding, etc. In one exemplary embodiment of the present invention, a liquid impervious layer may be bonded to a nonwoven fabric layer using a conventional point-bonding apparatus, wherein thermal bonds are used to join the liquid impervious layer to the nonwoven fabric layer. The degree of bonding, size of individual point bonds, and concentration of point bonds may vary as desired.

Fenestrations may be cut into any of the above-mentioned materials using conventional cutting processes including, but not limited to, a stamping process, etc.

III. Methods of Using Operating Room Coverings and Drapes

The present invention is further directed to methods of preparing a patient for a surgical procedure using the above-described coverings and/or drapes. In one exemplary embodiment of the present invention, the method of preparing a patient comprises the steps of removing a drape release liner to expose an outer adhesive layer on a covering or drape, placing the covering or drape over a patient so that the adhesive layer adheres to the patient and provides a view of a portion of the patient's body through an aperture in the drape, performing a surgical procedure, and covering the surgical site on the patient using a transparent cover.

This operation of the above-described embodiments of the present are believed to be readily apparent; however, a brief summation is provided below.

As described above, in one exemplary embodiment of the present invention, exemplary covering 10 may be used to cover an aseptic treatment site as described with reference to FIG. 2. As shown in FIG. 2, in this embodiment, exemplary covering 10 includes a substrate defining a first portion 44, which permits selective access to an aseptic treatment site on a patient and which defines an aperture 45; and a transparent cover 60 is borne by the substrate and which is removably affixed in substantially aseptic covering relation relative to the aperture 45. More particularly, exemplary covering 10 is suitable for covering aseptic treatment site 53 and includes a flexible substrate defining a first portion 44 having opposite first and second surfaces 50 and 51, and which defines an aperture 45, which permits access to aseptic treatment site 53 on the patient. Still further, a first adhesive region 52 is borne on second surface 51 of the flexible substrate defining first portion 44, and which substantially surrounds aperture 45. A flexible transparent cover 60 is moveably affixed on first surface 50 of first portion 44, and which is moveable along a course of travel 70 between a first, covering position 71 relative to aperture 45, and which permits observation of aseptic treatment site 53, to a second, uncovered position relative to aperture 45, and which permits access to aseptic treatment site 53. Further, a second adhesive region 66 is born by flexible, transparent cover 60, and which releasably adhesively affixes flexible transparent cover 60 to first surface 50 of first portion 44.

In this embodiment of the present invention, exemplary covering 10 for an aseptic treatment site 53 includes main body 30, having first region 41, and releasably detachable second region 42. First region 41 defines aperture 45, which permits access to aseptic treatment site 53 on a patient. First adhesive region 52 substantially surrounds aperture 45, and is borne by first region 41. First adhesive region 52 releasably adhesively affixes first region 41 on the body of the patient in an orientation such that first region 41 surrounds aseptic treatment site 53. Flexible transparent cover 60 is provided and hingedly affixed on first surface 50 of first region 41. Transparent cover 60 has a peripheral edge, opposite first and second surfaces 63 and 64, and opposite first and second ends 61 and 62. As seen in FIGS. 4-6, second end 62 of flexible transparent cover 60 is hingedly affixed on first surface 50. First end 61 is moveable along a substantially arcuately shaped path of travel 70 between (i) first position 71, wherein transparent cover 60 is disposed in a covering relation relative to aperture 45, and substantially out of direct contact with aseptic treatment site 53, and (ii) second position 72, wherein transparent cover 60 is disposed in an orientation, which allows access to aseptic treatment site 53 by way of aperture 45. Second adhesive region 66 is disposed on either one of transparent cover 60 or first region 41 to releasably adhesively affix transparent cover 60 in first covering position 71 relative to aperture 45. Second adhesive region 66 releases transparent cover 60 from first position 71 when sufficient force is applied to first end 61 of transparent cover 60. Second adhesive region 66 permits transparent cover 60 to be repeatedly moved between first and second positions 71 and 72 without substantially adhesively detaching first adhesive region 52 from the patient.

Therefore, it will be seen that the present invention provides many advantages over prior art surgical drapes, which have been utilized heretofore inasmuch as a clinician may maintain an aseptic treatment site long after a patient has been removed from a surgical theater by merely detaching second region 42 from first region 41, and thereafter observing the surgical intervention site through transparent cover 60 or 86. In the event that further intervention is required by the clinician, the patient may be moved back into a surgical theater and intervention may commence by removing transparent cover 60 or 86 without the need for further aseptic treatment of the site.

In a further embodiment of the present invention, a cover assembly, such as exemplary cover assembly 81, may be used to cover an aseptic treatment site as described with reference to FIGS. 9A-9D. As shown in FIG. 9A, in this embodiment, exemplary drape 80 may be placed over a patient (not shown) such that a surgical site on the patient is viewable through aperture 45. Following removal of drape release liner 108 (shown in FIG. 8) from drape 80, adhesive surface 93 of adhesive film 87 is used to adhere drape 80 to the patient. At this point, a surgical procedure may be performed on the patient. Following the surgical procedure, one or more components of cover assembly 81 are used to cover and protect the surgical site.

As shown in FIG. 9A, first release liner 85 and transparent cover 86 are separated from second release liner 97 of cover assembly 81. When present, as shown on exemplary first release liner 85, tab 83 may be used to grip first release liner 85. Tab 83 extends from first release liner 85 and is desirably substantially free of transparent cover 86 material (i.e., free of base film and adhesive material forming transparent cover 86). Once the combined structure of first release liner 85 and transparent cover 86 is completely separated from second release liner 97, the combined structure of first release liner 85 and transparent cover 86 may be placed over aperture 45 and bonded to areas of first region 41 surrounding aperture 45 as shown in FIG. 9B. Once the combined structure of first release liner 85 and transparent cover 86 is securely adhered to areas of first region 41 surrounding aperture 45, first release liner 85 may be peeled from transparent cover 86 as shown in FIG. 9C, leaving transparent cover 86 in place over aperture 45. Once the surgical site has been covered and protected, first region 41 may be detached from second region 42 along plurality of weakened areas or perforations 43 as shown in FIG. 9D.

FIG. 9D depicts first region 41 of exemplary drape 80 attached to patient body part 90, and covering aseptic treatment site 53. Transparent cover 86 provides visual inspection of aseptic treatment site 53, while preventing infection and/or contamination of aseptic treatment site 53 following the surgical procedure. The remaining portion of exemplary drape 80 (i.e., second region 42) may be discarded.

Figure 12B:
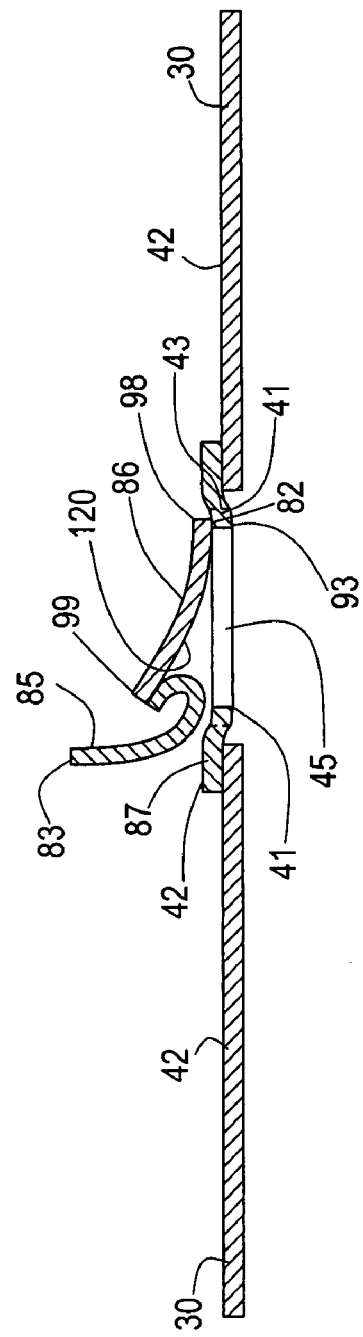

In yet a further embodiment of the present invention, a cover assembly similar to the exemplary cover assembly 81 as shown in FIGS. 12A-12D may be used to protect a surgical site (such as aseptic treatment site 53) following a surgical procedure. As shown in FIG. 12B, in this embodiment, exemplary drape 100 may be placed over a patient (not shown) such that a surgical site on the patient is viewable through aperture 45. Following removal of drape release liner 108 (shown in FIG. 12A) from drape 100, adhesive surface 93 of adhesive film 87 is used to adhere drape 100 to the patient. At this point, a surgical procedure may be performed on the patient. Following the surgical procedure, components of cover assembly 81 are used to cover and protect the surgical site.

As shown in FIGS. 12A-12B, first release liner 85 is peeled from transparent cover 86 using tab 83 to expose adhesive along surface 120 of transparent cover 86. As described above, tab 83 extends from first release liner 85 and is substantially free of transparent cover 86 material (i.e., base film and adhesive forming transparent cover 86). As first release liner 85 is separated from transparent cover 86 using tab 83, transparent cover 86 is moved into a position over aperture 45 as shown in FIG. 12B with surface 120 of transparent cover 86 facing aperture 45. Attached end 98 of transparent cover 86 remains stationary during this step, while unattached end 99 of transparent cover 86 moves to an opposite side of aperture 45 from first location 82.

When transparent cover 86 comprises a stretchable base film material as discussed above, first release liner 85 with tab 83 may be used to stretch transparent cover 86 over aperture 45 and any medical devices or materials (not shown) that may be present within the surgical area and designed to remain, at least temporarily, attached to and/or on the patient. Exemplary medical devices or materials that may be temporarily attached to a patient at aseptic treatment site 53 and/or covered by transparent cover 86 include, but are not limited to, gauze, tapes, sutures, an intravenous device, an introducer sheath, a needle, topographical medicines, a catheter, etc.

Once first release liner 85 is completely separated from transparent cover 86, transparent cover 86 may be bonded to areas of first region 41 surrounding aperture 45 as shown in FIG. 12C such that portions of surface 120 of transparent cover 86 are in contact with first region 41. Once the surgical site has been covered and protected, first region 41 may be detached from second region 42 along plurality of weakened areas or perforations 43 as shown in FIG. 12D.

FIG. 12D depicts first region 41 of exemplary drape 100 attached to patient body part 90, and covering aseptic treatment site 53. Transparent cover 86 provides visual inspection of aseptic treatment site 53, while preventing infection and/or contamination of aseptic treatment site 53 following the surgical procedure. The remaining portion of exemplary drape 100 (i.e., second region 42) may be discarded.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of an Operating Room Drape Having a Cover Assembly

An exemplary operating room drape as shown in FIG. 7 was prepared as follows. A polypropylene spunbonded fabric layer (BBA Nonwovens, Simpsonville, S.C.) having a basis weight of 61.0 grams per square meter (gsm) (1.8 ounce per square yard (osy)) was provided, and cut so as to have a length of 113.0 cm (44.5 in) and a width of 109.2 cm (43.0 in). An air-laid nonwoven fabric comprising bleached virgin wood pulp fibers and a polymer emulsion binder and having a basis weight of 97.0 gsm (2.9 osy) (Georgia Pacific, Atlanta, Ga., Product No. 396) was provided, and cut so as to have a length of 58.4 cm (23 in) and a width of 58.4 cm (23 in). The air-laid nonwoven fabric was adhesively bonded to a central portion of the polypropylene spunbonded fabric layer using a liquid adhesive comprising an ethylene vinyl acetate emulsion (H. B. Fuller). A circular fenestration having a fenestration diameter of 15.2 cm (6 in) was cut out of a central portion of the resulting laminate.

An adhesive tape (The 3M Company, St. Paul, Minn.) comprising (1) an adhesive film comprising a single coated adhesive tape having a matte finish, a film thickness of 76 µm (3 mil), a transparent polyethylene backing, and an acrylate pressure-sensitive adhesive layer on one side of the backing, and (2) a release liner temporarily protecting the adhesive layer and comprising a polyethylene coated Kraft paper having a silicone release agent on an outer surface thereof was provided. The adhesive tape had a length of 17.8 cm (7 in), a width of 17.8 cm (7 in), and a centrally located circular adhesive film fenestration therethrough with a fenestration diameter of 9.1 cm (3.6 in). The adhesive tape further comprised a centrally located circular pattern of perforations within the adhesive film, wherein the centrally located circular pattern of perforations had a diameter of 14.0 cm (5.5 in).

The release liner of the adhesive tape was removed, and the adhesive film of the adhesive tape was bonded to an upper surface of the air-laid nonwoven fabric so that the centrally located circular pattern of perforations was positioned within the circular fenestration of the above-described laminate. The release liner of the adhesive tape was then reattached to exposed areas of the adhesive film within the circular fenestration of the above-described laminate (i.e., the release liner was attached in a fashion similar to release liner 108 as shown in FIG. 8).

A substantially circular cover assembly comprising (i) a first upper release liner comprising a silicone-coated Kraft paper as describe above, (ii) a second lower release liner comprising a silicone-coated Kraft paper as describe above, and (iii) a transparent cover material positioned therebetween was adhesively bonded to an upper surface of the air-laid nonwoven fabric using the above-describe liquid adhesive. The transparent cover material comprised a polyurethane tape having a thickness of 0.05 mm (1.8 mil), which comprised (a) a 0.02 mm (0.8 mil) translucent polyurethane backing film and (b) an acrylate pressure-sensitive adhesive layer on an outer surface of the backing film (The 3M Company, St. Paul, Minn., Product Number 9842). The transparent cover material of the cover assembly had a circular shape and a diameter of about 12.7 cm (5 in).

The assembled drape was used during an operating procedure as shown in FIGS. 9A-9D. In particular, the release liner located on a lower surface of the drape was removed, and the drape was adhesively bonded to a patient so that a surgical site was viewable through the circular fenestration of the adhesive film. A surgical procedure was conducted. Upon completion of the surgical procedure, the transparent cover material along with the upper release liner were separated from the cover assembly and placed over the surgical site so that an outer periphery of the transparent cover material bonded to edges of the adhesive film along the adhesive film fenestration. The transparent cover material provided protection for the surgical site from infection and/or contamination. Then, the tear-away portion of the drape (i.e., the drape components outside of the centrally located circular pattern of perforations) was removed from the patient.

EXAMPLE 2

Preparation of an Operating Room Drape Having a Cover Assembly

An exemplary operating room drape as shown in FIG. 10 was prepared as follows. A polyester nonwoven fabric layer (Polymer Group, Inc., Greenville, S.C.) having a basis weight of 20.9 grams per square meter (gsm) (0.6 osy) was provided, and cut so as to have a length of 315.0 cm (124.0 in) and a width of 81.3 cm (32.0 in). A polyethylene film formed from a low density polyethylene resin (Winpak, Ltd., Minneapolis, Minn.) and having a film thickness of 45.7 μm (1.8 mil) was provided, and cut so as to have a length of 315.0 cm (124.0 in) and a width of 188.0 cm (74.0 in). An air-laid nonwoven fabric as used in Example 1 was provided, and cut so as to have a length of 315.0 cm (124.0 in) and a width of 85.1 cm (33.5 in).

The polyester nonwoven fabric layer was adhesively bonded to a central portion of a lower surface of the polyethylene film using the liquid adhesive described in Example 1. The air-laid nonwoven fabric was adhesively bonded to a central portion of an upper surface of the polyethylene film, opposite the polyester nonwoven fabric layer, using the liquid adhesive described in Example 1. The resulting structure had a three-layer main body portion, and perimeter portions (i.e., polyethylene film portions) extending along both sides of the drape (i.e., similar to the base construction shown in FIG. 10). A rectangular fenestration having a fenestration length of 22.9 cm (9 in) and a fenestration width of 15.2 cm (6 in) was cut out of a center portion of the resulting laminate about 71.1 cm (28 in) from one end (i.e., the head end) of the laminate.

An adhesive tape as described in Example 1 was provided except the adhesive tape had a rectangular shape, a length of 25.4 cm (10 in), a width of 17.8 cm (7 in), and a centrally located circular adhesive film fenestration therethrough with a fenestration diameter of 9.1 cm (3.6 in). The adhesive tape further comprised a centrally located rectangular of perforations within the adhesive film, wherein the centrally located rectangular pattern of perforations had a length of 21.8 cm (8.6 in), a width of 14.2 cm (5.6 in).

The release liner of the adhesive tape was removed, and the adhesive film of the adhesive tape was bonded to an upper surface of the air-laid nonwoven fabric so that the centrally located rectangular pattern of perforations was positioned within the rectangular fenestration of the above-described laminate. The release liner of the adhesive tape was then reattached to exposed areas of the adhesive film within the rectangular fenestration of the above-described laminate (i.e., the release liner was attached in a fashion similar to release liner 108 as shown in FIG. 12A).

A cover assembly comprising (i) a release liner (i.e., a silicone-coated Kraft paper as describe above), and (ii) a transparent cover material was adhesively bonded to an upper surface of the air-laid nonwoven fabric along an edge of the rectangular fenestration and within the rectangular pattern of perforations. A portion of the release liner of the cover assembly was peeled back exposing a portion of the adhesive on the transparent cover material so as to adhesively bond the cover assembly to the upper surface of the air-laid nonwoven fabric. The transparent cover material was the same material used in Example 1 except the transparent cover material had a rectangular shape, a length of 19.3 cm (7.6 in), a width of 11.2 cm (4.4 in), and an adhesive layer extending inward about 1.3 cm (about 0.5 in) from each edge of the transparent cover material The assembled drape was used during an operating procedure as shown in FIGS. 12A-12D. In particular, the release liner located on a lower surface of the drape was removed, and the drape was adhesively bonded to a patient so that a surgical site was viewable through the circular fenestration of the adhesive film. A surgical procedure was conducted. Upon completion of the surgical procedure, a tab portion of the release liner of the cover assembly was pulled to extend the transparent cover material over the surgical site so that an outer periphery of the transparent cover material bonded to edges of the adhesive film along the adhesive film fenestration. The transparent cover material provided protection for the surgical site from infection and/or contamination. Then, the tear-away portion of the drape (i.e., the drape components outside of the rectangular pattern of perforations) was removed from the patient.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A disposable drape comprising:

a first region of drape material having a first region outer periphery and at least one fenestration positioned within the first region outer periphery, wherein the first region is suitable for covering an aseptic treatment site and the at least one fenestration is sized so as to surround the aseptic treatment site so that the aseptic treatment site is accessible through the at least one fenestration;

a second region of drape material surrounding the outer first region periphery of the first region, said second region of drape material being detachably joined to the drape material of the first region such that detachment of the second region from the first region does not alter an outer periphery of the at least one fenestration; and a cover assembly located on a first location of the drape, wherein the cover assembly comprises (i) a first release liner, and (ii) a transparent cover having a transparent cover outer periphery and being releasably attached to the first release liner, said transparent cover having a first adhesive layer on a lower surface of the transparent cover opposite the first release liner, said first adhesive layer being bonded to the drape at the first location.

2. The disposable drape of claim 1, wherein the first region and the second region are separated from one another by a plurality of weakened areas that form a pattern of perforations.

3. The disposable drape of claim 2, wherein the pattern of perforations forms a line along the first region outer periphery, said line being positioned at least a minimal distance, $d_m$, from an edge of the at least one fenestration.

4. The disposable drape of claim 2, wherein the pattern of perforations forms a line along the first region outer periphery, said line being positioned substantially an equal distance from any point along an edge of the at least one fenestration.

5. The disposable drape of claim 1, wherein the lower surface of the transparent cover has a first area that is substantially free of adhesive, and a second area comprising the first adhesive layer, said second area extending along at least a portion of the transparent cover outer periphery.

6. The disposable drape of claim 5, wherein said first area has a first area surface area and shape, said at least one fenestration has a fenestration surface area and shape, and said first area surface area and shape are substantially similar to said fenestration surface area and shape.

7. The disposable drape of claim 1, wherein the first location is positioned proximate the at least one fenestration and within the first region of the drape, said transparent cover being sized so as to extend over the at least one fenestration and adhesively bond to areas of the first region surrounding the at least one fenestration such that the transparent cover outer periphery surrounds the at least one fenestration.

8. The disposable drape of claim 1, wherein the cover assembly further comprises (iii) a second release liner positioned on the drape at the first location, said first adhesive layer being releasably bonded to the second release liner.

9. The disposable drape of claim 8, wherein the first location is positioned within the first region or the second region of the drape.

10. The disposable drape of claim 1, further comprising a second adhesive layer on a back side of the drape material of the first region for releasably adhering the drape to a patient, said second adhesive layer surrounding the at least one fenestration.

11. The disposable drape of claim 10, further comprising a third release liner positioned on an outer surface of the second adhesive layer.

12. A disposable drape comprising:
a first region of drape material having a first region outer periphery and at least one fenestration positioned within the first region outer periphery, wherein the first region is suitable for covering an aseptic treatment site so that the aseptic treatment site is accessible through the at least one fenestration; and a cover assembly located on a single outer surface of the drape at a first location of the drape, wherein the cover assembly comprises (i) a transparent cover having a transparent cover outer periphery and comprising a first adhesive layer on an outer surface of the transparent cover, at least a portion of said first adhesive layer being bonded to the drape at the first location, and (ii) a first release liner releasably attached to portions of said first adhesive layer of said transparent cover, wherein the outer surface of the transparent cover has a first area that is substantially free of adhesive, and a second area comprising the first adhesive layer, said second area extending along at least a portion of the transparent cover outer periphery.

13. The disposable drape of claim 12, wherein the first location is positioned proximate the at least one fenestration and within the first region of the drape, said transparent cover being sized so as to extend over the at least one fenestration and adhesively bond to areas of the first region surrounding the at least one fenestration such that the transparent cover outer periphery surrounds the at least one fenestration.

14. The disposable drape of claim 12, further comprising a second region of drape material surrounding the first region outer periphery of the first region, said second region of drape material being detachably joined to the drape material of the first region by a plurality of weakened areas that form a pattern of perforations around the first region outer periphery.

15. The disposable drape of claim 14, wherein the first location is positioned proximate the at least one fenestration and within the first region of the drape, said transparent cover being sized so as to extend over the at least one fenestration and adhesively bond to areas of the first region surrounding the at least one fenestration such that the transparent cover outer periphery surrounds the at least one fenestration.

16. A disposable drape comprising:
a first region of drape material having a first region outer periphery and at least one fenestration positioned within the first region outer periphery, wherein the first region is suitable for covering an aseptic treatment site so that the aseptic treatment site is accessible through the at least one fenestration; and a cover assembly located on a first location of the drape, wherein the cover assembly comprises (i) a first release liner, and (ii) a transparent cover having a transparent cover outer periphery and being releasably attached to the first release liner via an upper surface of the transparent cover, said transparent cover having a first adhesive layer on a lower surface of the transparent cover opposite the first release liner, said cover assembly being releasably bonded to the drape at the first location via said first adhesive layer.

17. The disposable drape of claim 16, further comprising a second release liner positioned on the drape at the first location, said first adhesive layer of said transparent cover being releasably bonded to the second release liner.

18. The disposable drape of claim 17, wherein (i) the first release liner and an upper surface of the transparent cover are releasably bonded to one another with a first bond strength, (ii) the first adhesive layer of the transparent cover and the second release liner are releasably bonded to one another with a second bond strength, and (iii) said first bond strength is greater than said second bond strength.

19. The disposable drape of claim 16, further comprising a second region of drape material surrounding the first region outer periphery of the first region, said second region of drape material being detachably joined to the drape material of the first region by a plurality of weakened areas that form a pattern of perforations around the first region outer periphery.

20. The disposable drape of claim 19, wherein said first location is positioned along a surface of said second region.

21. The disposable drape of claim 16, wherein said cover assembly is located away from said at least one fenestration so as not to cover any portion of said at least one fenestration.

22. A method of covering an aseptic treatment site, said method comprising the steps of:
   positioning the disposable drape of claim 1 over the aseptic treatment site such that the aseptic treatment site is accessible through the at least one fenestration;
   covering the aseptic treatment site with the transparent cover so as to bond the transparent cover, to areas of the drape material of the first region surrounding the at least one fenestration such that the transparent cover outer periphery encompasses an outer periphery of the at least one fenestration; and
   detaching the second region from the first region.

23. The method of claim 22, further comprising:
   after said positioning step and prior to said covering step, performing a surgical procedure on the aseptic treatment site.

24. A method of covering an aseptic treatment site, said method comprising the steps of:
   positioning the disposable drape of claim 13 over the aseptic treatment site such that the aseptic treatment site is accessible through the at least one fenestration;
   extending the transparent cover from the first location into a position over the at least one fenestration such that the transparent cover outer periphery extends around an outer periphery of the at least one fenestration; and
   bonding the first adhesive layer of the transparent cover to areas of the drape material of the first region surrounding the at least one fenestration such that the transparent cover outer periphery encompasses an outer periphery of the at least one fenestration.

25. The method of claim 24, further comprising:
   after said positioning step and prior to said extending step, performing a surgical procedure on the aseptic treatment site.

26. A method of covering an aseptic treatment site, said method comprising the steps of:
   positioning the disposable drape of claim 17 over the aseptic treatment site such that the aseptic treatment site is accessible through the at least one fenestration;
   separating the first release liner and transparent cover from the second release liner at the first location;
   bonding the first adhesive layer of the transparent cover to areas of the drape material of the first region surrounding the at least one fenestration such that the transparent cover outer periphery encompasses an outer periphery of the at least one fenestration; and
   separating the first release liner from the transparent cover.

27. The method of claim 26, further comprising:
   after said positioning step and prior to said bonding step, performing a surgical procedure on the aseptic treatment site.

* * * * *